United States Patent
Yoshikawa et al.

(10) Patent No.: US 11,486,875 B2
(45) Date of Patent: *Nov. 1, 2022

(54) METHOD FOR MEASURING CHOLESTEROL UPTAKE CAPACITY OF LIPOPROTEINS

(71) Applicant: SYSMEX CORPORATION, Kobe (JP)

(72) Inventors: Keiko Yoshikawa, Kobe (JP); Amane Harada, Kobe (JP); Katsuhiro Murakami, Kobe (JP); Maria Kiriyama, Kobe (JP); Keiko Miwa, Kobe (JP); Takuya Kubo, Kobe (JP)

(73) Assignee: SYSMEX CORPORATION, Kobe (JP)

(*) Notice: Subject to any disclaimer, the term of this patent is extended or adjusted under 35 U.S.C. 154(b) by 101 days.

This patent is subject to a terminal disclaimer.

(21) Appl. No.: 17/023,946

(22) Filed: Sep. 17, 2020

(65) Prior Publication Data

US 2021/0003562 A1 Jan. 7, 2021

Related U.S. Application Data

(63) Continuation of application No. 15/650,414, filed on Jul. 14, 2017, now Pat. No. 10,809,249, which is a continuation of application No. PCT/JP2016/065753, filed on May 27, 2016.

(30) Foreign Application Priority Data

| May 29, 2015 | (JP) | 2015-110510 |
| Sep. 30, 2015 | (JP) | 2015-193648 |
| Oct. 20, 2015 | (JP) | 2015-206422 |
| Mar. 9, 2016 | (JP) | 2016-046069 |

(51) Int. Cl.
| G01N 33/53 | (2006.01) |
| G01N 33/92 | (2006.01) |
| G01N 33/50 | (2006.01) |
| G01N 33/543 | (2006.01) |
| G01N 33/58 | (2006.01) |
| C12Q 1/60 | (2006.01) |
| G01N 33/00 | (2006.01) |

(52) U.S. Cl.
CPC .......... G01N 33/5044 (2013.01); C12Q 1/60 (2013.01); G01N 33/5008 (2013.01); G01N 33/5038 (2013.01); G01N 33/53 (2013.01); G01N 33/543 (2013.01); G01N 33/58 (2013.01); G01N 33/92 (2013.01); G01N 33/00 (2013.01); G01N 2800/044 (2013.01)

(58) Field of Classification Search
CPC .......... C12Q 1/60; G01N 33/53; G01N 33/58; G01N 33/92; G01N 33/00; G01N 2800/044

See application file for complete search history.

(56) References Cited

U.S. PATENT DOCUMENTS

| 10,436,806 B2* | 10/2019 | Harada | G01N 33/92 |
| 10,809,249 B2* | 10/2020 | Yoshikawa | G01N 33/5044 |
| 2016/0109469 A1 | 4/2016 | Harada et al. | |

FOREIGN PATENT DOCUMENTS

| EP | 3009844 A1 | 4/2016 |
| JP | 2004-354284 A | 12/2004 |
| JP | 2008-139299 A | 6/2008 |
| JP | 2011-184374 A | 9/2011 |
| JP | 2015-20969 A | 2/2015 |
| WO | 9936785 A1 | 7/1999 |
| WO | 2012/104411 A1 | 8/2012 |

OTHER PUBLICATIONS

Gaibelet et al. (Biochemical and Biophysical Research Communications 440 (2013) 533-538) (Year: 2013).*
Chinese Office Action dated Apr. 4, 2019 in a counterpart Chinese patent application No. 201680010462.9.
Gaibelet et al., "21-Methylpyrenyl-cholestrol stably and specifically associates with lipoprotein peripheral hemi-membrane: A new labelling tool", Biochemical and Biophysical Research Communications, 2013, vol. 440, pp. 533-538 (total 6 pages).
Avanti Polar Lipids, Inc. "Various Fluorescent Labelled Cholesterols," 2010 (retrieved from the following URL: http://www.funakoshi.co.jp/contens/3960) 3 pages total.
Wustner D. et al., "Quantitative assessment of sterol traffic in living cells by dual labeling with dehydroergosterol and BODIPY-cholesterol," Chemistry and Physics of Lipids, vol. 164, 2011, p. 221-235 (15 pages total).
Agnoletto, Doctoral Candidate, "Effects of oxysterols on cell survival and proliferation pathways in human endothelial cells," 2008, pp. 1-108. (Year: 2008).
Meyer et al. (Biospektrum, vol. 18, pp. 142-145, published 2012) (Year: 2012).
Ana Jonas, et al., "Incorporation of Excess Cholesterol by High Density Serum Lipoproteins", Biochimica et Biophysica Acta, 1978, pp. 47-57, vol. 528, No. 1.
Amit V. Khera, M.D., et al., "Cholesterol Efflux Capacity, High-Density Lipoprotein Function, and Atherosclerosis", The New England Journal of Medicine, Jan. 13, 2011, pp. 127-135, vol. 364, No. 2.
International Search Report for PCT/JP2016/065753 dated Aug. 16, 2016 [PCT/ISA/210].
Written Opinion for PCT/JP2016/065753 dated Aug. 16, 2016 [PCT/ISA/237].
Communication, dated Aug. 31, 2021, issued by the Japanese Patent Office in counterpart Japanese Machine Patent Application No. 2020-047833.

(Continued)

Primary Examiner — Tracy Vivlemore
Assistant Examiner — Nam P Nguyen
(74) Attorney, Agent, or Firm — Sughrue Mion, PLLC

(57) ABSTRACT

The present invention relates to a method for measuring the cholesterol uptake capacity of lipoproteins. The present invention also relates to a reagent kit for measuring the cholesterol uptake capacity of lipoproteins. The present invention further relates to a tagged cholesterol which can be used in the method and the reagent kit.

19 Claims, 8 Drawing Sheets

(56) References Cited

OTHER PUBLICATIONS

Communication, dated Oct. 19, 2020, issued by the European Patent Office in corresponding European Patent Application No. 19 205 325.4.
Communication, dated Apr. 6, 2021, issued by the Japanese Patent Office in counterpart Japanese Machine Patent Application No. 2020-047833.
First Office Action dated Jun. 17, 2022 issued by the Chinese Patent Office in Chinese Application No. 201910889578.X.

* cited by examiner

METHOD FOR MEASURING CHOLESTEROL UPTAKE CAPACITY OF LIPOPROTEINS

CROSS-REFERENCE TO RELATED APPLICATIONS

This application is a continuation of U.S. patent application Ser. No. 15/650,414, filed Jul. 14, 2017, which is a continuation of International Application No. PCT/JP2016/065753, filed May 27, 2016, which claims priority to Japanese Patent Application No. 2015-110510, filed May 29, 2015, Japanese Patent Application No. 2015-193648, filed Sep. 30, 2015, Japanese Patent Application No. 2015-206422, filed Oct. 20, 2015, and Japanese Patent Application No. 2016-046069, filed Mar. 9, 2016. The entire disclosures of the prior applications are considered part of the disclosure of the accompanying continuation application, and are hereby incorporated by reference.

The present invention relates to a method for measuring the cholesterol uptake capacity of lipoproteins. The present invention also relates to a reagent kit for measuring the cholesterol uptake capacity of lipoproteins. The present invention further relates to a tagged cholesterol which can be used in the method and the reagent kit.

BACKGROUND ART

Cholesterol metabolic disorder is involved in various diseases, and the blood cholesterol concentration is known to be an indicator of the disorder. However, the cholesterol concentration may not reflect the presence of the diseases, the risk of the diseases, and the like. Therefore, there is interest in the qualitative indicator which is focused on the functions of cholesterols as well as the quantitative indicator such as the cholesterol concentration.

For example, even if the high-density lipoprotein cholesterol (HDL-C) concentration in blood is high, the risk of the cardiovascular disease (CVD) may not be decreased. Therefore, the possibilities in which the HDL-C concentration does not reflect the risk of CVD completely are pointed out. There is interest in the functions of high-density lipoprotein (HDL). It is reported that the excretion of cholesterol from peripheral tissues by HDL is a negative prognostic factor against the risk of CVD.

As a method for determining the functions of HDL, for example, PCT International Application Publication No. 2012/104411 describes a method for diagnosing dyslipidemia by using a fluorescently labeled cholesterol without using cultured cells. In the method, a monolayer surrounding the various lipoprotein including low-density lipoprotein (LDL) or HDL is labeled with a fluorescently labeled cholesterol (cholesterol pyrene), and a subject is diagnosed with dyslipidemia based on the resulting fluorescent spectrum by measuring the labeled lipoprotein. The literature describes that the labeled lipoprotein can be separated from free fluorescently labeled cholesterol by ultracentrifugal separation, dialysis, or FPLC by using gel filtration column.

SUMMARY

The present invention provides a method for measuring the cholesterol uptake capacity of lipoproteins, comprising the steps of:

forming a complex by contacting a lipoprotein in a sample, a tagged cholesterol, and an antibody which specifically binds to the lipoprotein, the complex comprising the lipoprotein, the tagged cholesterol incorporated into the lipoprotein, and the antibody;

labeling the complex by bonding a capture body which specifically binds to the tag and a label with the complex;

detecting a signal resulted from the label which has been bound to the complex.

The present invention also provides a reagent kit for measuring the cholesterol uptake capacity of lipoproteins, comprising:

a tagged cholesterol;
an antibody which specifically binds to the lipoprotein;
a capture body which specifically binds to the tag; and
a label.

The present invention also provides a tagged cholesterol represented by the following formula (III):

[Chemical Formula 1]

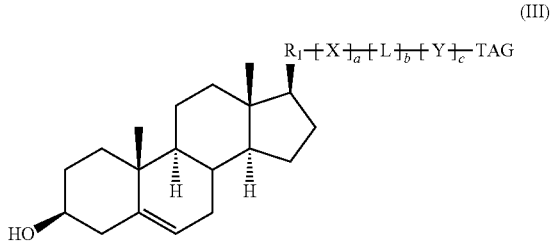

(III)

where $R_1$ is an alkylene group having 1 to 6 carbon atoms, which may have a methyl group, X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$R_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—, wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;

L represents —$(CH_2)_d$—[$R_3$—$(CH_2)_e$]$_f$— or —[$(CH_2)_e$—$R_3$]$_f$—$(CH_2)_d$—, wherein $R_3$ is an oxygen atom, a sulfur atom, —NH—, —NH—(C=O)—, or —(C=O)—NH—;

TAG is a tag;

a and c are identical or different and each represents an integer of 0 to 6;

b is 0 or 1;

d and e are identical or different and each represents an integer of 0 to 12; and f is an integer of 0 to 24.

DESCRIPTION OF EMBODIMENTS

Figure 1:
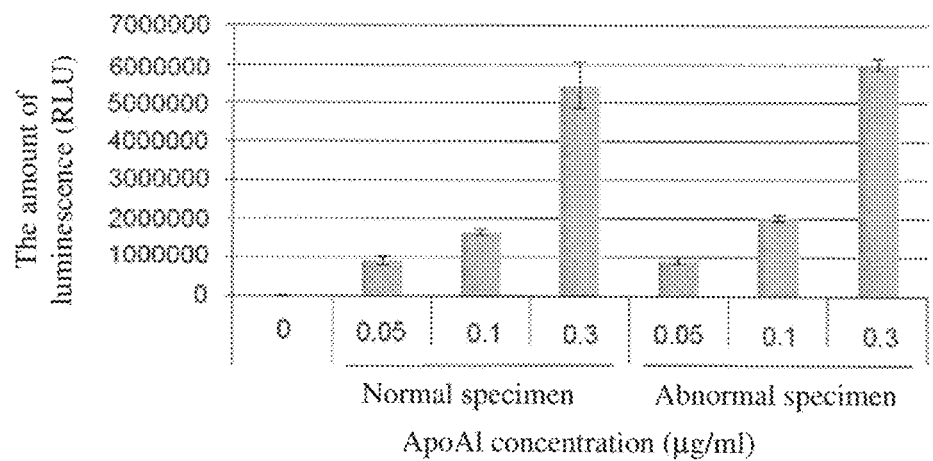
FIG. 1 is a graph showing the amount of the complex captured by an anti-apolipoprotein AI (ApoAI) antibody on the solid phase, as measured by sandwich ELISA method.

In the method for measuring the cholesterol uptake capacity of lipoproteins of the embodiment of the invention (hereinafter, referred to as simply "measuring method"), a tagged cholesterol is directly incorporated into a lipoprotein in a sample, as described below, and therefore the method does not require cholesterol-containing cells such as macrophages as used in conventional method for measuring the function of HDL to excrete cholesterol from the cells. Accordingly, the measuring method of the embodiment of the invention can be performed in a cell-free system in all steps as described below. The cell-free system means that cells are not needed for the method of measuring the cholesterol uptake capacity of lipoproteins. That is, the measuring method of the embodiment of the invention can be performed without utilizing the properties and functions of cells for the measuring method. In the embodiment, even if the sample contains cells originated from the subject, the measuring method is considered to be in a cell-free system because the cells themselves almost have no effect on the incorporation of the tagged and labeled cholesterol into the lipoprotein.

The principle of the detection of the tagged cholesterol incorporated into the lipoprotein in the measuring method of the embodiment of the invention is as follows. When the lipoprotein is contacted with the tagged cholesterol, the tagged cholesterol is esterified and incorporated into the lipoprotein. Cholesterol incorporated into the lipoprotein is transferred from the surface layer of the lipoprotein particle to the central moiety. In the tagged cholesterol, cholesterol moiety is incorporated into the lipoprotein, and the tag is probably exposed on the outer surface of the lipoprotein. The phrase "outer surface of the lipoprotein" refers to the outer surface of the lipoprotein particle. The phrase "exposed on the outer surface" means the presence on the outer surface of the lipoprotein and the protrusion from the outer surface of the lipoprotein. In the embodiment, cholesterol incorporated into the lipoprotein is detected by bonding the tag exposed on the outer surface and the capture body which specifically binds to the tag. Each step in the measuring method of the present embodiment will now be described.

In the measuring method of the embodiment, a lipoprotein in a sample, a tagged cholesterol, and an antibody which specifically binds to the lipoprotein are firstly contacted to form a complex containing the lipoprotein, the tagged cholesterol incorporated into the lipoprotein, and the antibody.

In the embodiment, the sample is not particularly limited as long as the sample contains a lipoprotein of mammals, preferably, of human. Examples of the sample include blood samples such as blood, serum and plasma.

The lipoprotein to be measured in the embodiment may be HDL, LDL, intermediate-density lipoprotein (IDL), very low-density lipoprotein (VLDL), or chylomicron (CM). HDL is the lipoprotein having a density of 1.063 g/mL or more. LDL is the lipoprotein having a density of 1.019 g/mL or more and less than 1.063 g/mL. IDL is the lipoprotein having a density of 1.006 g/mL or more and less than 1.019 g/mL. VLDL is the lipoprotein having a density of 0.95 g/mL or more and less than 1.006 g/mL. CM is the lipoprotein having a density of less than 0.95 g/mL.

In the measuring method of the present embodiment, the blood sample can be separated by any known method including ultracentrifugal separation or polyethylene glycol (PEG) precipitation method to obtain a fraction containing a selected lipoprotein.

In the embodiment, the blood sample and the selected fraction of lipoprotein can be diluted with an aqueous medium, and the resulting diluted liquid is used as the sample for adjusting the lipoprotein concentration. Examples of the aqueous medium include water, and a buffer including a physiological saline, a phosphate buffered saline (PBS), and Tris-HCl. Since the indicator of the lipoprotein concentration in the sample is the concentration of the main component of the lipoprotein, ApoAI, in the embodiment, a part of the sample may be taken and measured for the ApoAI concentration by any known immunoassay (for example, immunonephelometry). The lipoprotein concentration in the sample can be adjusted based on the measured ApoAI concentration.

For example, a blocking agent such as bovine serum albumin (BSA) or liposome may optionally be added to the sample. Since it is known that the lipoprotein incorporates cholesterol after the esterification of cholesterol, a fatty acid or a composition containing thereof (for example, liposome) required for the esterification reaction of cholesterol by the lipoprotein may be added to the sample.

In the embodiment, the tagged cholesterol is used as cholesterol incorporated into the lipoprotein. The tagged cholesterol refers to the cholesterol in which a tag is bound directly or indirectly via a linker at any position of alkyl chains (at C20-C27) which is bound at C17 of the naturally occurring cholesterol. The cholesterol moiety of the tagged cholesterol may have the structure of the naturally occurring cholesterol, or may have the structure of the cholesterol in which one or more methylene group and/or methyl group is eliminated from alkyl chains which is bound at C17 of the naturally occurring cholesterol (also referred to as norcholesterol).

The tag added to cholesterol is not particularly limited as long as it does not inhibit the incorporation of cholesterol by the lipoprotein and a material which can be specifically bound to the tag (it is the same as "the capture body which specifically binds to the tag" as described below) is present or obtained.

As described above, since the lipoprotein incorporates cholesterol after the esterification of cholesterol, more preferably, the tagged cholesterol which is esterified with the lipoprotein is used. In the method of the embodiment, the tagged cholesterol is esterified by lecithin-cholesterol acyltransferase (LCAT), in the sample when it contacts with the sample. The method for confirming the esterification of the tagged cholesterol by the lipoprotein is known in the art, and the method can be routinely performed by those skilled in the art.

In the embodiment, the tag may be a naturally occurring material or a synthesized material. Examples of the tag include a compound, a peptide, a protein, a nucleic acid, and combination thereof. The compound may be any known label compound in the art as long as a material which can be specifically bound to the compound is present or obtained. An example of the compound is a coloring compound.

In the art, it is known that the liposolubility of cholesterol is increased by the esterification of cholesterol, and the incorporation of cholesterol by the lipoprotein is facilitated. The tag added to cholesterol may be a liposoluble material or a hydrophobic material.

Examples of the combination of the tag and the material which can be specifically bound to the tag include an antigen and an antibody which recognizes the antigen; a hapten and an anti-hapten antibody; a peptide or a protein and an aptamer which recognizes them; a ligand and its receptor; an oligonucleotide and an oligonucleotide having the complementary strand; biotin and avidin (or streptavidin); a histidine tag (a peptide containing a histidine of 6 to 10 residues) and nickel; and glutathione-S-transferase (GST) and glutathione. The antigen as the tag may be a peptide tag and a protein tag known in the art. Examples of the antigen include FLAG®, hemagglutinin (HA), Myc protein, and green fluorescent protein (GFP). Example of the hapten as the tag includes 2,4-dinitrophenol.

Example of the tag includes the tag having the structure represented by the following formula (I):

[Chemical Formula 2]

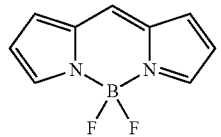

(I)

or the tag having the structure represented by the following formula (II).

[Chemical Formula 3]

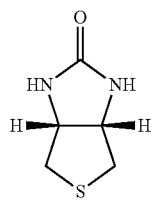

(II)

The structure represented by the formula (I) is boron dipyrromethene (BODIPY®) backbone. The structure represented by the formula (II) shows a part of biotin. The tagged cholesterol containing the structure represented by the formula (I) or (II) is preferred because capture bodies against the tags are generally available. The tagged cholesterol having 2,4-dinitrophenyl (DNP) group is also preferred because the anti-DNP antibody is commercially available.

Example of the tagged cholesterol includes the tagged cholesterol represented by the following formula (III):

[Chemical Formula 4]

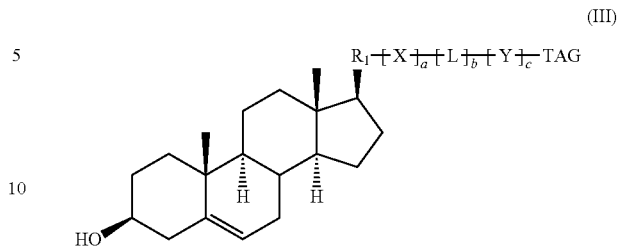

(III)

wherein $R_1$ is an alkylene group having 1 to 6 carbon atoms, which may have a methyl group, X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$R_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—, wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;

L represents —$(CH_2)_d$—[$R_3$—$(CH_2)_e$]$_f$— or —[$(CH_2)_e$—$R_3$]$_f$—$(CH_2)_d$—, wherein $R_3$ is an oxygen atom, a sulfur atom, —NH—, —NH—(C=O)—, or —(C=O)—NH—;

TAG is a tag;

a and c are identical or different and each represents an integer of 0 to 6;

b is 0 or 1;

d and e are identical or different and each represents an integer of 0 to 12; and f is an integer of 0 to 24.

In the formula (III), when a, b and c are all 0, the tagged cholesterol represented by the formula has no linker, and the tag and the cholesterol moiety are bonded directly. In the formula (III), when any one of a, b and c is not 0, the tagged cholesterol represented by the formula has a linker (—[X]$_a$-[L]$_b$-[Y]$_c$—) between the tag and the cholesterol moiety. It is believed that the linker facilitates the bonding between the tag exposed on the outer surface of the lipoprotein and the capture body. Each substituent group in the formula (III) will now be described.

$R_1$ has an alkylene group having 1 to 6 carbon atoms as the main chain, and may have a methyl group at any position. $R_1$ corresponds to the alkyl chain which is bound at C17 of the naturally occurring cholesterol. In the embodiment, when $R_1$ has 1 to 5 carbon atoms, preferred $R_1$ has a methyl group at C20 of the naturally occurring cholesterol. When $R_1$ has 6 carbon atoms, preferred $R_1$ has the same structures as alkyl chains at C20-C27 of the naturally occurring cholesterol.

[X]$_a$ corresponds to a connecting moiety between $R_1$ and L, [Y]$_c$ or the tag. [Y]$_c$ corresponds to a connecting moiety between $R_1$, [X]$_a$ or L and the tag. X and Y are determined depending on the type of reaction bonding between the cholesterol moiety and the linker and the type of reaction bonding between the linker and the tag.

In $R_2$, the atomic bonding refers to the direct bonding without intervening any other atom. When $R_2$ is an alkylene group having 1 to 10 carbon atoms, examples of the alkylene group include methylene, ethylene, propylene, isopropylene, butylene, isobutylene, pentylene, neopentylene, hexylene, heptylene, octylene, 2-ethylhexylene, nonylene, and decylene group. Among them, an alkylene group having 1 to 4 carbon atoms is preferred. When $R_2$ is an alkylene group having a substituent group, the number of the carbon atoms as described above does not include that of the carbon atoms in the substituent group.

When $R_2$ is an arylene group or a heteroarylene group, the group may be an aromatic ring having 6 to 12 carbon atoms which may include one or more hetero atoms selected from N, S, O, and P. Examples of the group include phenylene, naphthylene, biphenylylene, furanylene, pyrrolene, thiophenylene, triazolene, oxadiazolene, pyridylene, and pyrimidylene group. When $R_2$ is an arylene group or a heteroarylene group having a substituent group, the number of the carbon atoms as described above does not include that of the carbon atoms in the substituent group.

When $R_2$ is a cycloalkylene group or a heterocycloalkylene group, the group may be a non-aromatic ring having 3 to 8 carbon atoms which may include one or more hetero atoms selected from N, S, O, and P. Examples of the group include cyclopropylene, cyclobutylene, cyclopentylene, cyclohexylene, cycloheptylene, cyclooctylene, pyrrolidinylene, piperidinylene, and morpholinylene. When $R_2$ is a cycloalkylene group or a heterocycloalkylene group having a substituent group, the number of the carbon atoms as described above does not include that of the carbon atoms in the substituent group.

Examples of the substituent group in $R_2$ include hydroxyl, cyano, alkoxy, =O, =S, $-NO_2$, $-SH$, halogen, haloalkyl, heteroalkyl, carboxyalkyl, amine, amide, and thioether group. $R_2$ may have a plurality of the substituent groups. Halogen represents fluorine, chlorine, bromine, or iodine. Alkoxy represents —O-alkyl group. The alkyl group is a linear or branched saturated aliphatic hydrocarbon group having 1 to 5 carbon atoms, preferably 1 or 2 carbon atoms.

Preferably, a and c are both 1, X and Y are identical or different and each represents —(C=O)—NH— or —NH—(C=O)—.

L corresponds to a spacer which has a polymer structure that adds a predetermined length to the linker. The preferred polymer structure moiety has properties that do not inhibit the incorporation of cholesterol by the lipoprotein and the preferred linker has properties that has difficulty in the incorporation of the linker into the lipoprotein. Example of the polymer includes a hydrophilic polymer such as polyethylene glycol (PEG). In a preferred embodiment, L is a structure represented by $-(CH_2)_2-[O-(CH_2)_e]f-$ or $-[(CH_2)_e-O]f-(CH_2)_d-$. d and e are identical or different and each represents an integer of 0 to 12, preferably an integer of 2 to 6, and more preferably d and e are both 2. f is an integer of 0 to 24, preferably an integer of 2 to 11, and more preferably an integer of 4 to 11.

Example of the tagged cholesterol without the linker includes a fluorescently labeled cholesterol (23-(dipyrromethene boron difluoride)-24-norcholesterol) represented by the following formula (IV):

[Chemical Formula 5]

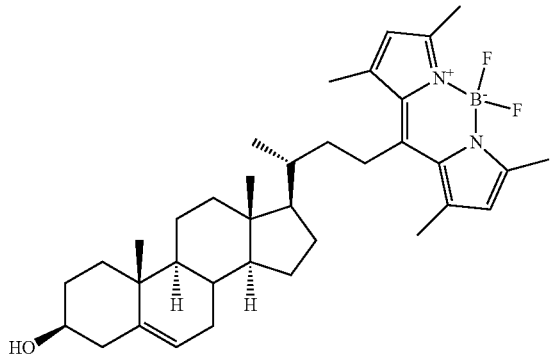

(IV)

The fluorescently labeled cholesterol is commercially available (Trade Name TopFluor Cholesterol, CAS No: 878557-19-8, Avanti Polar Lipids, Inc.). In the tagged cholesterol represented by the following formula (IV), the tag (the fluorescent moiety having BODIPY backbone structure) is directly bonded at C23 of cholesterol. As an example of the capture body which specifically binds to the fluorescent moiety having BODIPY backbone structure, an anti-BODIPY antibody (BODIPY FL Rabbit IgG Fraction, A-5770, Life technologies Corporation) is commercially available.

Example of the tagged cholesterol in which the tag is bound via a linker includes a biotin-tagged cholesterol represented by the following formula (V):

[Chemical Formula 6]

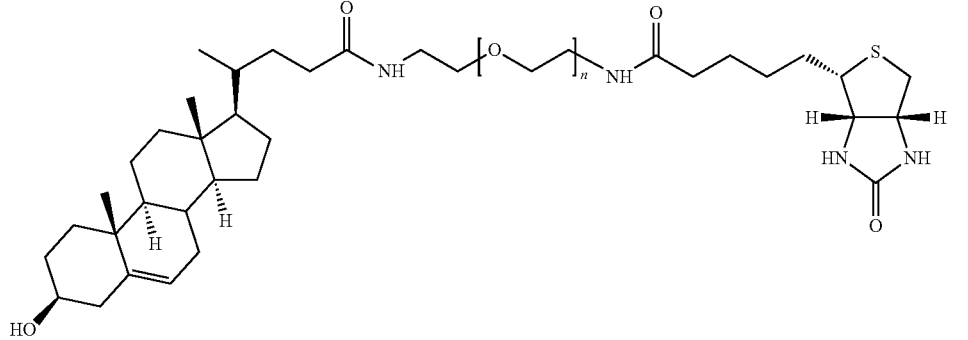

(V)

wherein, n is an integer of 0 to 24, preferably an integer of 2 to 11, and more preferably an integer of 4 to 11. In the tagged cholesterol, the tag (the biotin moiety represented by the formula (II)) is bonded to the cholesterol moiety via the linker (polyethylene glycol). A suitable capture body which specifically binds to the biotin moiety is avidin or streptavidin. An avidin or streptavidin bound to a label such as horseradish peroxidase (HRP) or alkaline phosphatase (ALP) is also commercially available.

Example of the tagged cholesterol includes DNP-tagged cholesterol represented by the following formula (VI):

[Chemical Formula 7]

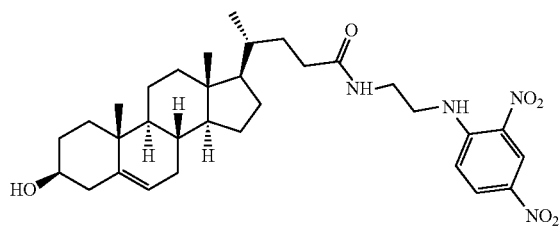

(VI)

In the tagged cholesterol, DNP is bound to the cholesterol moiety via the linker (—(C=O)—NH—$CH_2$—$CH_2$—NH—). A suitable capture body which specifically binds to DNP is an anti-DNP antibody. An anti-DNP antibody bound to a label such as HRP or ALP is also commercially available.

Although the bonding form of the cholesterol moiety and the tag is not particularly limited, the cholesterol moiety and the tag may be bonded, or the cholesterol moiety and the tag may be bonded via a linker. Although the bonding means is not particularly limited, for example, a crosslink by utilizing a functional group is preferred because it is convenient. Although the functional group is not particularly limited, an amino group, a carboxyl group and a sulfhydryl group are preferred because commercially available crosslinkers can be used.

Since cholesterol has no functional group in the alkyl chain bonded at C17, the cholesterol derivative having a functional group in the alkyl chain is preferably used for the addition of the tag. Examples of the cholesterol derivative include a precursor of bile acid and a precursor of steroids. Specific preferred examples of the cholesterol derivative include 3β-hydroxy-Δ5-cholenoic acid, 24-amino-5-colen-3β-ol. The functional group of the tag varies depending on the type of the tag. For example, when a peptide or a protein is used as the tag, an amino group, a carboxyl group and a sulfhydryl group (SH group) can be used. When biotin is used as the tag, a carboxyl group in the side chain can be used. The preferred linker is a polymer compound having functional groups at both terminals. When biotin is added as the tag, a commercially available biotin labeling agent can be used. The reagent contains biotin to which various length of spacer arms (for example, PEG) having a functional group such as an amino group at the terminal are bound.

Exemplary crosslink reaction of the functional group will be described below. A compound having an amino group as the functional group can crosslink with a compound having N-hydroxysuccinimide (NHS) ester or an isothiocyano group as the reactive group (see the following Figure). For example, when cholesterol having an amino group and a tag having an amino group are crosslinked, a crosslink reagent or a linker having NHS esters at both terminals can be used.

[Chemical Formula 8]

Reaction of an NHS ester with an amino group

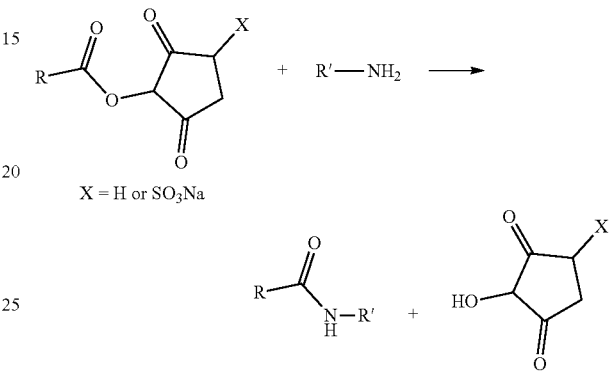

X = H or $SO_3Na$

Reaction of an isothiocyano group with an amino group

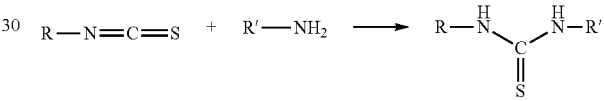

A compound having a carboxyl group as the functional group is firstly reacted with a compound having a carbodiimide group (—N=C=N—). (See the following Figure. In the Figure, reacted with1-ethyl-3-(3-dimethylaminopropyl)carbodiimide hydrochloride.) Then the mixture is reacted with NHS to form the unstable NHS ester. Then the ester can be reacted with a compound having an amino group to crosslink with the compound having a carboxyl group. For example, when cholesterol having a carboxyl group and a tag having an amino group are crosslinked, they can crosslink in the method. When cholesterol having a carboxyl group and a tag having a carboxyl group are crosslinked, a crosslink reagent or a linker having amino groups at both terminals can be used.

[Chemical Formula 9]

(First step)

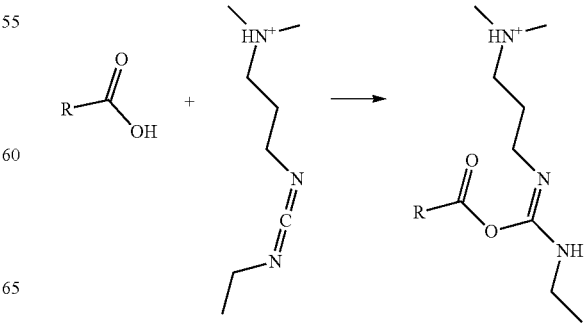

(Second step)

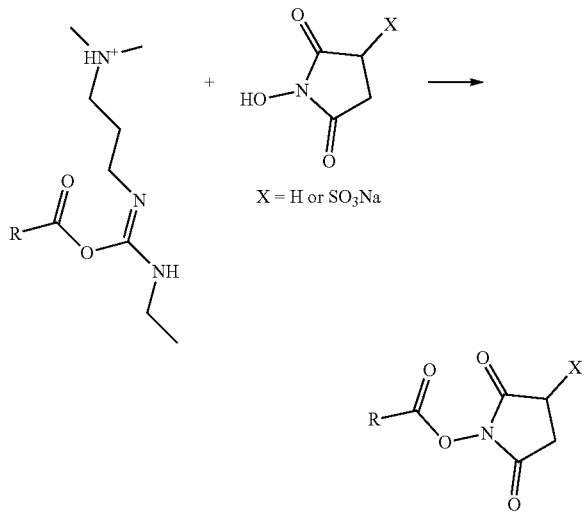

X = H or SO₃Na (Third step)

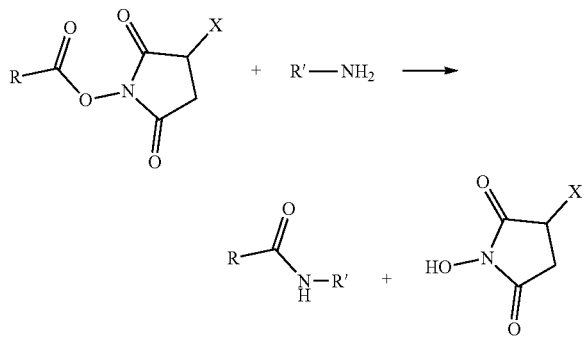

A compound having a sulfhydryl group as the functional group can crosslink with a compound having a maleimide group or bromo (or iodo) acetamide group as the reactive group (see the following Figure). When cholesterol having a sulfhydryl group and a tag having a sulfhydryl group are crosslinked, a crosslink reagent or a linker having maleimide at both terminals can be used.

[Chemical Formula 10]

Reaction of a maleimide group with a sulfhydryl group

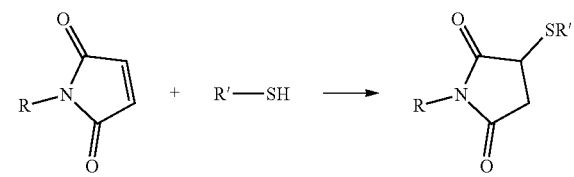

Reaction of a bromo (iodo) acetamide group with a sulfhydryl group

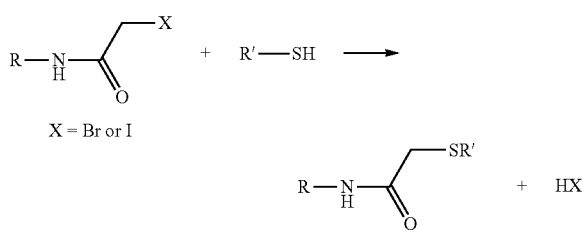

X = Br or I

These crosslink reactions can be performed under ordinary temperature and normal pressure. The solvent used in the reaction is not particularly limited as long as it is inert for the reactions, and it can dissolve or disperse each compound added in the reaction. Examples of the solvent includes aromatic hydrocarbons such as benzene, toluene, and xylene; ethers such as diethylether, tetrahydrofuran, ethylene glycol dimethyl ether, and 1,4-dioxane; amides such as N,N-dimethylformamide; a sulfoxide such as dimethyl sulfoxide; halogenated hydrocarbons such as dichloromethane and chloroform. The solvent can be used alone or the mixture of the solvent can be used.

In the embodiment, the antibody which specifically binds to the lipoprotein (hereinafter, also referred to as "anti-lipoprotein antibody") is not particularly limited as long as it is an antibody which can be specifically bound to a part of the surface of the lipoprotein. Preferably, the antibody is the antibody which can be specifically bound to the apolipoprotein, which is a component of the lipoprotein. Examples of the antibody include an anti-ApoAI antibody and an anti-ApoAII antibody. Among them, an anti-ApoAI antibody is particularly preferred. In the embodiment, a commercially available anti-lipoprotein antibody and anti-ApoAI antibody can be used.

The anti-lipoprotein antibody may be a monoclonal antibody or a polyclonal antibody. The origin of the antibody is not particularly limited, and the antibody may be an antibody originated from mammal such as mouse, rat, hamster, rabbit, goat, horse, and camel. The isotype of the antibody may be IgG, IgM, IgE, or IgA, and IgG is preferred. In the embodiment, as the anti-lipoprotein antibody, the fragment and derivative thereof can be used. Examples include the Fab fragment and the F(ab')2 fragment.

When the anti-ApoAI antibody is used as the anti-lipoprotein antibody, the lipoprotein in which the tagged cholesterol is incorporated may be treated with an oxidant before the lipoprotein is contacted with the anti-ApoAI antibody. The action of the oxidant can improve the reactivity of the anti-ApoAI antibody and the lipoprotein. Examples of the oxidant include hydrogen peroxide, peroxynitrite, chlorine dioxide, and hypochlorous acid.

In the embodiment, contacting the lipoprotein in the sample, the tagged cholesterol, and the anti-lipoprotein antibody can be performed by mixing the sample containing the lipoprotein, the tagged cholesterol solution, and the anti-lipoprotein antibody solution, for example. After mixing, the lipoprotein starts to incorporate the tagged cholesterol, and a complex of the lipoprotein in which the tagged cholesterol is incorporated and the anti-lipoprotein antibody is formed.

The order of contacting the lipoprotein in the sample, the tagged cholesterol, and the anti-lipoprotein antibody is not particularly limited. They may be mixed simultaneously or sequentially. In the embodiment, preferably, the lipoprotein and the tagged cholesterol are firstly mixed and the tagged cholesterol is incorporated into the lipoprotein, and then the anti-lipoprotein antibody is contacted with them. If the tagged cholesterol and anti-lipoprotein antibody is firstly contacted, the tagged cholesterol bound to the anti-lipoprotein antibody may have difficulty in the incorporation of the cholesterol into the lipoprotein.

In the embodiment, although the added amount of the tagged cholesterol is not particularly limited, some excess of the tagged cholesterol may be added so that the tagged cholesterol is not depleted. For example, the tagged cholesterol can be added to the sample so that the final concentration is from 0.1 to 30 μm, and preferably from 1 to 10 μm.

The added amount of the anti-lipoprotein antibody is not particularly limited, and the amount can be suitably selected depending on the type of the antibody and the like by those skilled in the art.

Although the temperature and time for contacting is not particularly limited, the mixed liquid of the sample, the tagged cholesterol, and the anti-lipoprotein antibody can be incubated at 20-48° C., preferably at 25-42° C. for 1 minute to 24 hours, preferably 10 minutes to 2 hours. During the incubation, the mixed liquid may be left to stand, or stirred or shaken.

When the lipoprotein and the tagged cholesterol are firstly mixed, the mixed liquid can be incubated at 20-48° C., preferably at 25-42° C. for 1 minute to 24 hours, preferably 10 minutes to 2 hours. After that, the anti-lipoprotein antibody is added to the mixed liquid, and can be incubated at 20-48° C., preferably at 25-42° C. for 1 minute to 24 hours, preferably 10 minutes to 2 hours. During the incubation, the mixed liquid may be left to stand, or stirred or shaken.

In the embodiment, the complex of the lipoprotein in which the tagged cholesterol is incorporated and the anti-lipoprotein antibody may form on the solid phase. In the case, for example, the sample containing the lipoprotein, the tagged cholesterol solution, the anti-lipoprotein antibody solution and the solid phase may be contacted. Alternatively, after the sample containing the lipoprotein, the tagged cholesterol solution and the anti-lipoprotein antibody solution are mixed, the resulting mixed liquid and the solid phase may be contacted. Alternatively, the anti-lipoprotein antibody which was previously fixed on the solid phase may be used. For example, the complex can be formed on the solid phase by contacting the solid phase having fixed anti-lipoprotein antibody with a mixed liquid of the sample containing the lipoprotein and the tagged cholesterol solution. Although the temperature and time of contacting is not particularly limited, for example, the similar conditions as in the step of forming the complex as described above.

The preferred solid phase is the solid phase being capable of capturing the anti-lipoprotein antibody in the complex. The type of the solid phase is not particularly limited, and examples of the solid phase include a solid phase made by a physically adsorbing material of the antibody, and a solid phase having a fixed molecule which specifically binds to the antibody. Examples of the molecule which specifically binds to the antibody include protein A or G, and an antibody which specifically recognizes the antibody (i.e., a secondary antibody). Also, the combination of the material intervening between the antibody and the solid phase may be used to bond between them. Examples of the combination include a combination of biotin and avidin (or streptavidin); and a combination of a hapten and an anti-hapten antibody. For example, when the anti-lipoprotein antibody was previously modified with biotin, the solid phase having fixed avidin or streptavidin can capture the antibody.

As materials for the solid phase, an organic polymer compound, an inorganic compound, a biopolymer, and the like can be selected. Examples of the organic polymer compound include a latex, polystyrene, polypropylene, styrene-methacrylic acid copolymer, styrene-glycidyl (meta) acrylate copolymer, styrene-styrene sulfonate copolymer, methacrylic acid polymer, acrylic acid polymer, acrylonitrile butadiene styrene copolymer, vinyl chloride-acrylate ester copolymer, and polyvinyl acetate acrylate. Examples of the inorganic compound include magnetic materials (iron oxide, chromic oxide, cobalt and ferrite), silica, alumina, and glass. Examples of the biopolymer include insoluble agarose, insoluble dextran, gelatin, and cellulose. Two or more of these materials may be used in combination therewith. The shape of the solid phase is not particularly limited, and examples of the shape include a particle, a microplate, a microtube, and a test tube. Among them, a microplate and a particle are preferred. A 96-well microplate and a magnetic particle are particularly preferred.

In the embodiment, the B/F separation step for removing an unreacted free component which has not formed the complex may be performed after the step of forming the complex as described above and before the step of labeling the complex as described below. The unreacted free component refers to a component which is not the component of the complex. Examples of the unreacted free component include a free tagged cholesterol which was not incorporated into the lipoprotein, and a free anti-lipoprotein antibody which did not bind to the lipoprotein. Although the means of the B/F separation is not particularly limited, the complex can be separated from the unreacted free component by collecting the complex only, for example, with ultracentrifugal separation. When the complex is formed on the solid phase, if the solid phase is a particle, the complex can be separated from the unreacted free component by collecting the particle capturing the complex only. When the solid phase is a container such as a microplate or a microtube, the complex can be separated from the unreacted free component by removing a liquid containing the unreacted free component. After removing the unreacted free component, the collected complex may be washed with a suitable aqueous medium such as PBS.

In the measuring method of the embodiment of the invention, the complex is labelled by bonding the capture body which specifically binds to the tag and the label to the produced complex.

The capture body which specifically binds to the tag may be suitably determined depending on the type of the tag of the tagged cholesterol. For example, with reference to the combination of the tag and the material which can specifically bind to the tag, the capture body can be selected from an antibody, a ligand receptor, an oligonucleotide, biotin, avidin (or streptavidin), a histidine tag or nickel, GST or glutathione. Among them, the preferred capture body is an antibody which specifically binds to the tag. The antibody may be a commercially available antibody, or an antibody produced by any method known in the art. The antibody may be a monoclonal antibody or a polyclonal antibody. The origin and isotype of the antibody is not particularly limited, and is similar to description about the anti-HDL antibody. The fragment and derivative of the antibody can be used. Examples include the Fab fragment and the F(ab')2 fragment.

As the label, a material which generates a signal (hereinafter, also referred to as "signal generating material") and a material which generates a detectable signal by catalyzing the reaction of other material can be used. Exemplary examples of the signal generating material include fluorescent material and radioisotope. An example of the material which generates a detectable signal by catalyzing the reaction of other material is an enzyme. Examples of the enzyme include peroxidase, alkaline phosphatase, β-galactosidase, glucose oxidase, tyrosinase, acid phosphatase, and luciferase. Examples of the fluorescent material include a fluorochrome such as fluorescein isothiocyanate (FITC), rhodamine, Alexa Fluor®, cyanine based colorant; and a fluorescent protein such as GFP. Examples of the radioisotope include $^{125}$I, $^{14}$C, and $^{32}$P. Among them, the preferred label is an enzyme, and peroxidase and alkaline phosphatase are particularly preferred.

In a preferred embodiment, the complex is labeled by indirectly bonding the label and the complex via the capture body which specifically binds to the tag. Examples include binding the complex and the capture body which binds to the label, or binding the label and the capture body which binds to the complex. In this case, the capture body which was previously bound to the label may be used, or a label which can specifically bind to the capture body may be used.

For example, the capture body which was previously bound to the label can be obtained by labeling the capture body which specifically binds to the tag with the label. The method for labeling a material is known in the art. When the capture body is an antibody, the capture body may be labeled with a commercially available labeling kit. Example of the label which can specifically bind to the capture body includes a labeled antibody which specifically recognizes the capture body (i.e., a secondary antibody).

Although the temperature and time conditions of the step of labeling are not particularly limited, the mixture of the complex, the capture body which specifically binds to the tag, and the label can be incubated at 4-60° C., preferably at 25-42° C. for 1 second to 24 hours, preferably 10 minutes to 2 hours. During the incubation, the mixture may be left to stand, or stirred or shaken.

In the embodiment, the B/F separation step for removing an unreacted free component which has not been bound to the complex may be performed after the step of labeling the complex as described above and before the step of detecting the signal as described below. Examples of the unreacted free component include a free capture body which did not bind to the tag, and a free label which did not bind to the capture body. The means of the B/F separation is not particularly limited, and is as similar as described in the B/F separation performed after the step of forming the complex and before the step of labeling the complex.

In the measuring method of the embodiment of the invention, a signal resulted from the label which has been bound to the complex is detected. "Detect a signal" includes detecting the presence or absence of the signal qualitatively, quantifying the signal strength, and detecting the signal semi-quantitatively as a plurality of levels, for example, "no signal", "weak", and "strong". Since the signal reflects the amount of the tagged cholesterol incorporated into the lipoprotein, the detecting result of the signal is an indicator of the cholesterol uptake capacity of the lipoprotein. Therefore, the above measuring method can be called as the method for evaluating the cholesterol uptake capacity of the lipoprotein based on the lipoprotein in which the tagged cholesterol is incorporated and the signal resulted from the complex with the anti-lipoprotein antibody.

The method for detecting the signal resulted from the label is known in the art. In the embodiment, a suitable measuring method can be selected depending on the type of the signal resulted from the label. For example, when the label is an enzyme, the measuring method can be performed by measuring the signal such as light or color generated by reacting the substrate for the enzyme with an instrument known in the art. Examples of the instrument include spectrophotometer and luminometer.

The substrate for the enzyme can be suitably selected from known substrates depending on the type of the enzyme. For example, when peroxidase is used as the enzyme, examples of the substrate include a chemiluminescent substrate such as luminol and derivative thereof; and a chromogenic substance such as 2,2'-azinobis (3-ethylbenzothiazoline-6-sulfonic acid ammonium) (ABTS), 1,2-phenylene diamine (OPD), 3,3',5,5'-tetramethylbenzidine (TMB). When alkaline phosphatase is used as the enzyme, examples of the substrate include a chemiluminescent substrate such as CDP-Star® (4-chloro-3-(methoxyspiro[1,2-dioxetane-3, 2'-(5'-chloro)tricyclo[3.3.1.13,7]decane]-4-yl)phenyl phosphate disodium), CSPD® (3-(4-methoxyspiro[1,2-dioxetane-3,2-(5'-chloro)tricyclo[3.3.1.13,7] decane]-4-yl) phenyl phosphate disodium); and a chromogenic substance such as 5-bromo-4-chloro-3-indolyl phosphoric acid (BCIP), 5-bromo-6-chloro-indolyl phosphate disodium, and p-nitrophenyl phosphoric acid.

When the label is a radioisotope, the radiation as the signal can be measured by using an instrument known in the art such as a scintillation counter. When the label is a fluorescent material, the fluorescence as the signal can be measured by using an instrument known in the art such as a fluorescence microplate reader. The excitation wavelength and the fluorescent wavelength can be suitably determined depending on the type of the fluorescent material used.

In a further embodiment, the result of the cholesterol uptake capacity of the lipoprotein obtained from the measuring method may be utilized for diagnosing whether the subject has dyslipidemia or not. That is, a method for assisting the diagnosis of dyslipidemia comprising the following steps is provided:

forming a complex by contacting a lipoprotein obtained from the subject, a tagged cholesterol, and an antibody which specifically binds to the lipoprotein, the complex containing the lipoprotein, the tagged cholesterol incorporated into the lipoprotein, and the antibody;

labeling the complex by bonding a capture body which specifically binds to the tag and a label with the complex;

detecting a signal resulted from the label which has been bound to the complex; and obtaining information about dyslipidemia of the subject based on the result of the step of detecting.

By collecting data of the measured signal obtained from the sample of the healthy subject and the dyslipidemia patient according to the measuring method as described above, a threshold value or a reference range for the cholesterol uptake capacity of lipoprotein can be determined. By comparing the threshold value or the reference range with the measured signal when the specimen of the subject is used, information about dyslipidemia of the subject, that is, information whether the cholesterol uptake capacity of lipoprotein of the subject is normal or within the reference range can be obtained. Based on the information, the diagnosis whether the subject has dyslipidemia or not can be assisted.

The reagent kit used for the measuring method as described above is encompassed in the scope of the present invention. That is, provided is the reagent kit for measuring the cholesterol uptake capacity of lipoproteins (hereinafter, referred to as simply "reagent kit"), comprising a tagged cholesterol; an antibody which specifically binds to the lipoprotein (an anti-lipoprotein antibody); a capture body which specifically binds to the tag; and a label. When the label is an enzyme, the reagent kit of the present embodiment may further contain a substrate for the enzyme.

Figure 3A:
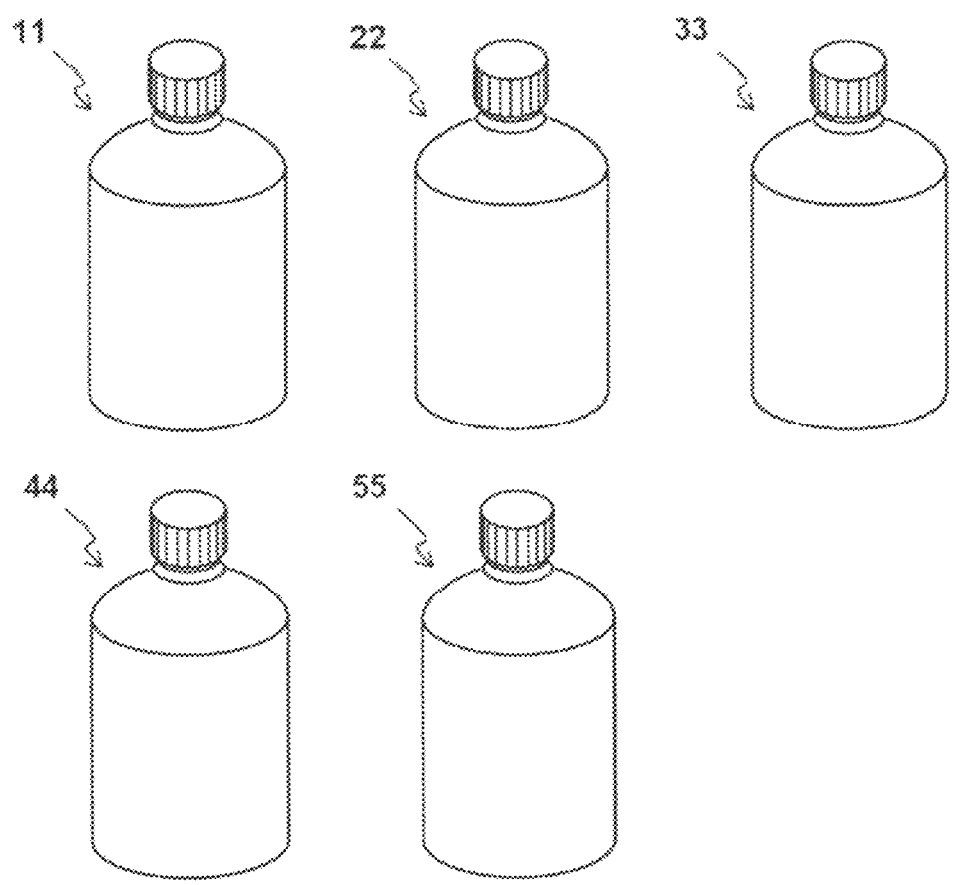
FIG. 3A is a figure showing an example of an appearance of the reagent kit according to the present embodiment.

The form of the tagged cholesterol, the anti-lipoprotein antibody, the capture body which specifically binds to the tag, the label, and the substrate is not particularly limited. The form may be solid (for example, powder, crystal, and lyophilized product) or liquid (for example, solution, suspension, and emulsion). In the embodiment, preferably, the tagged cholesterol, the anti-lipoprotein antibody, the capture body which specifically binds to the tag, the label, and the substrate are each stored in a separate container, or are individually packaged. The details of type and handling of the sample, the tagged cholesterol, the antibody which specifically binds to the lipoprotein, the capture body which specifically binds to the tag, the label, and the substrate of the enzyme are similar to the description of the measuring method. FIG. 3A shows an example of an appearance of the reagent kit of the present embodiment. In the Figure, 11 shows a first container containing the tagged cholesterol. 22 shows a second container containing the anti-lipoprotein antibody. 33 shows a third container containing the capture body which specifically binds to the tag. 44 shows a fourth container containing the enzyme as the label. 55 shows a fifth container containing the chemiluminescent substrate for the enzyme.

Figure 3B:
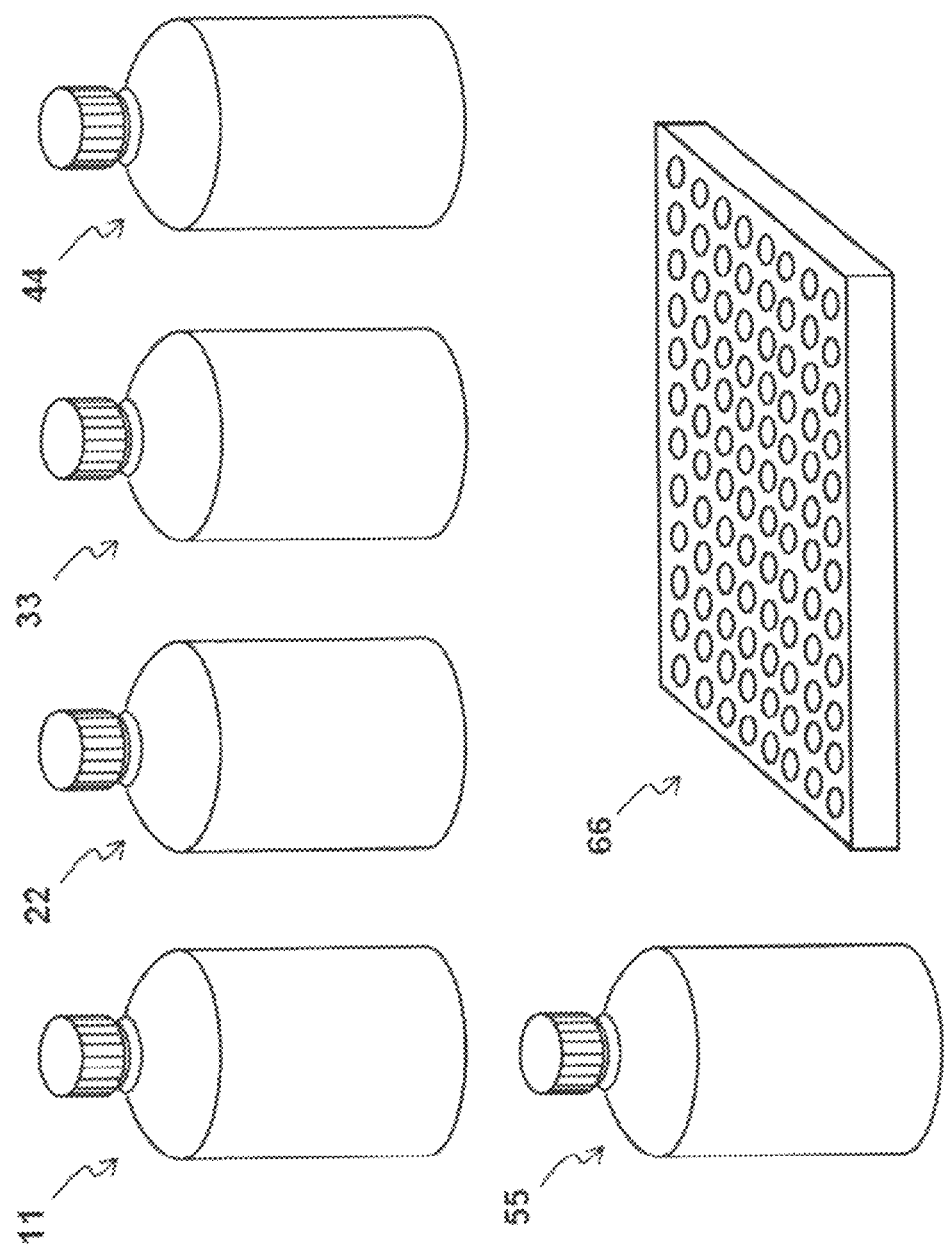
FIG. 3B is a figure showing an example of an appearance of the reagent kit according to the present embodiment.

The reagent kit may further contain a solid phase for fixing the anti-lipoprotein antibody. In this case, preferably, the tagged cholesterol, the anti-lipoprotein antibody, the capture body which specifically binds to the tag, the label, the substrate, and the solid phase are each stored in a separate container, or are individually packaged. FIG. 3B shows an example of an appearance of the reagent kit including the solid phase. The detail of the solid phase is similar to the description of the measuring method. In the Figure, 66 shows a 96-well microplate as the solid phase.

Figure 3C:
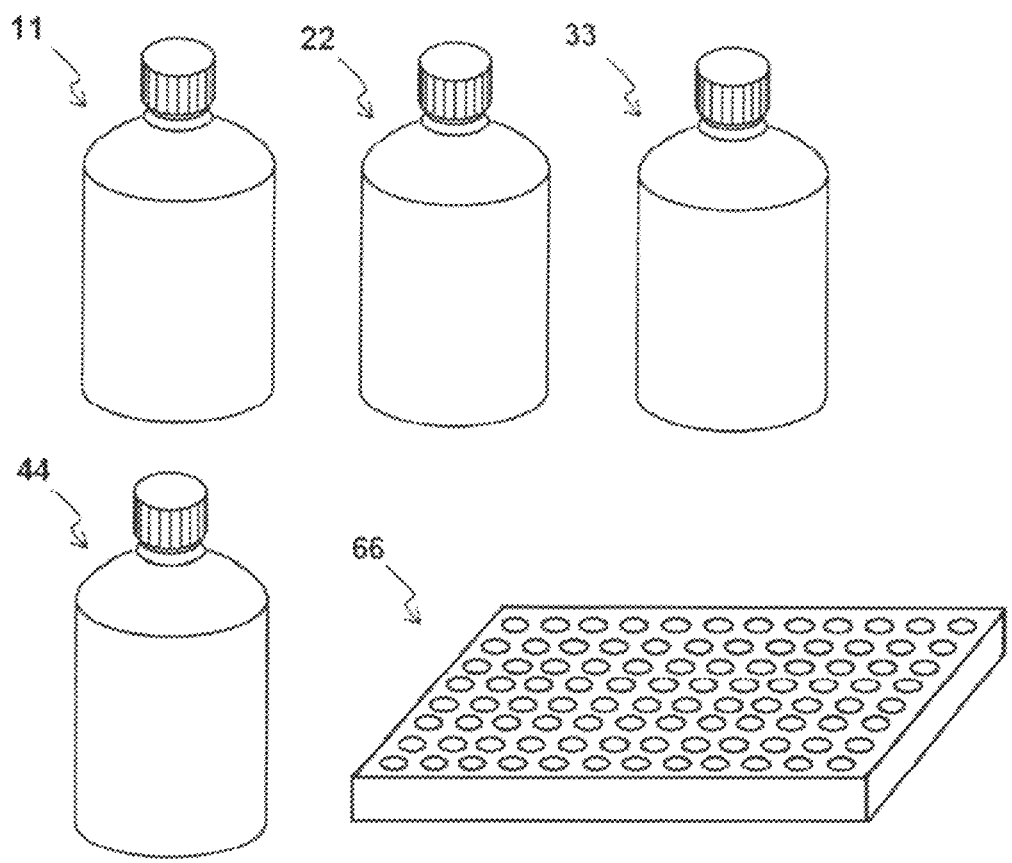
FIG. 3C is a figure showing an example of an appearance of the reagent kit according to the present embodiment.

In the embodiment, the anti-lipoprotein antibody, preferably the anti-ApoAI antibody, may be previously fixed on the solid phase. In the case, the reagent kit may be composed of the tagged cholesterol, the capture body which specifically binds to the tag, the label, the substrate, the solid phase, and the anti-lipoprotein antibody fixed on the solid phase. FIG. 3C shows an example of an appearance of the reagent kit. In the Figure, 11 shows a first container containing the tagged cholesterol. 22 shows a second container containing the capture body which specifically binds to the tag. 33 shows a third container containing the enzyme as the label. 44 shows a fourth container containing the chemiluminescent substrate for the enzyme. 66 shows a solid phase (96-well microplate) for fixing an antibody which binds to a lipoprotein.

Figure 3D:
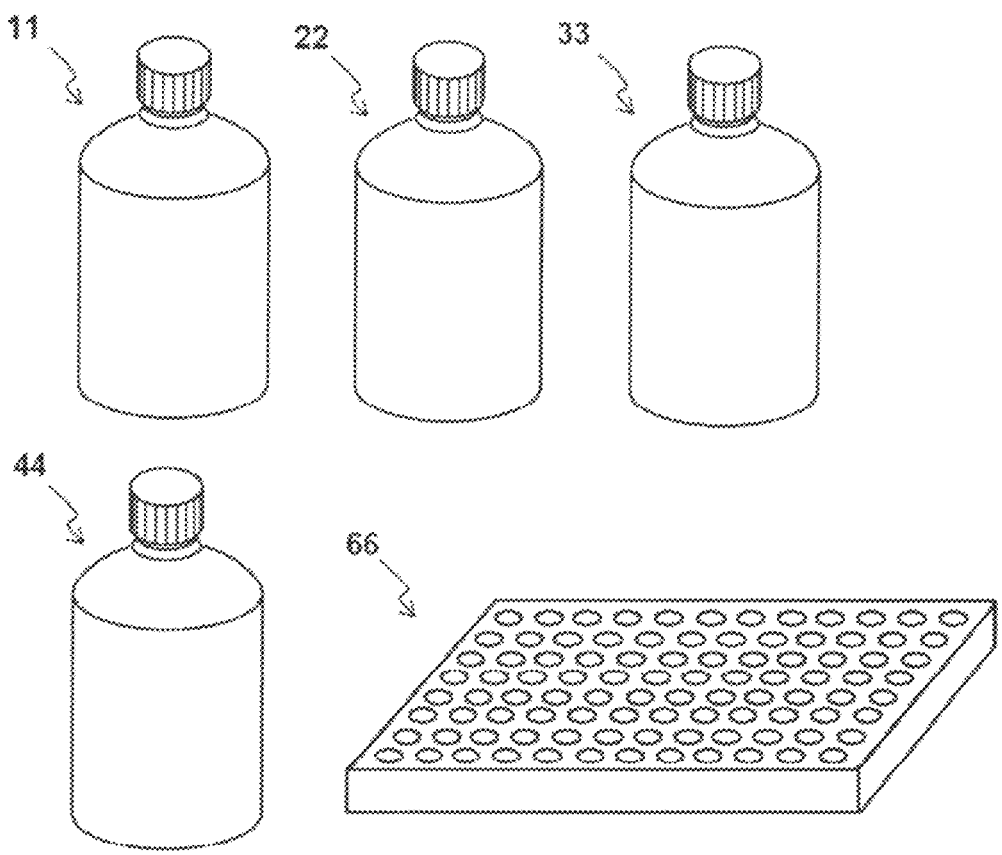
FIG. 3D is a figure showing an example of an appearance of the reagent kit according to the present embodiment.

In the embodiment, the label may be previously bound to the capture body which specifically binds to the tag (the resulting capture body is also referred to as "labeled capture body"). In the case, the reagent kit may be composed of the tagged cholesterol, the anti-lipoprotein antibody, the labeled capture body, the substrate, and the solid phase. FIG. 3D shows an example of an appearance of the reagent kit. In the Figure, 11 shows a first container containing the tagged cholesterol. 22 shows a second container containing the anti-lipoprotein antibody. 33 shows a third container containing the capture body bound to the enzyme as the label. 44 shows a fourth container containing the chemiluminescent substrate for the enzyme. 66 shows a solid phase (96-well microplate).

Figure 3E:
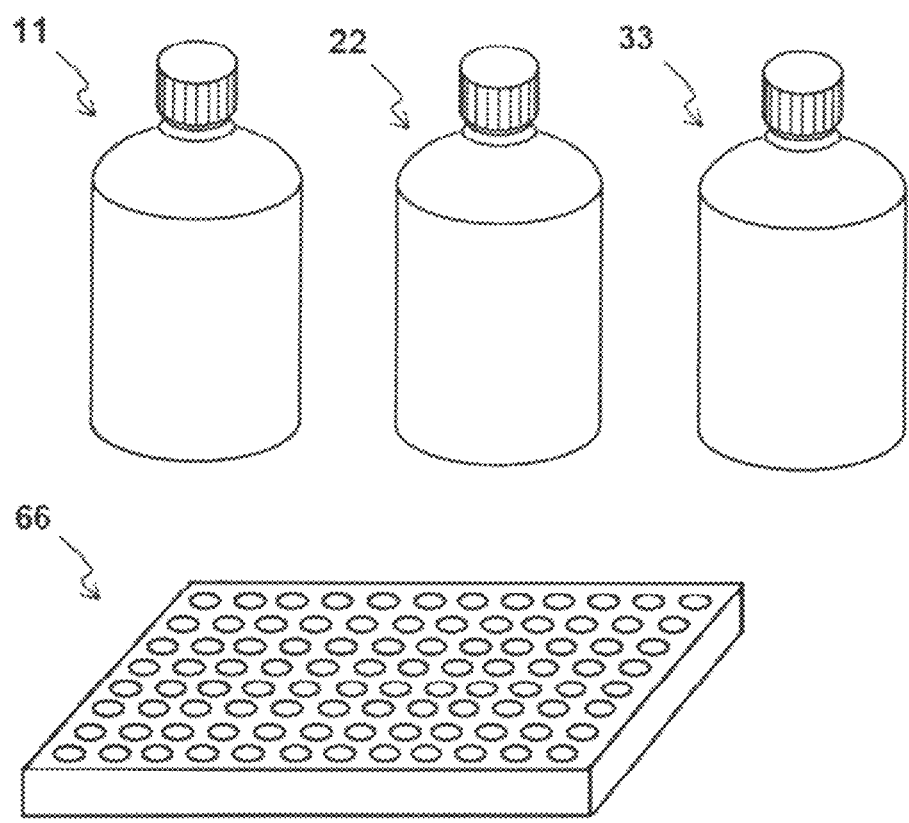
FIG. 3E is a figure showing an example of an appearance of the reagent kit according to the present embodiment.

Further, the anti-lipoprotein antibody, preferably the anti-ApoAI antibody, may be previously fixed on the solid phase. In the case, the reagent kit may be composed of the tagged cholesterol, the labeled capture body, the substrate, and the anti-lipoprotein antibody fixed on the solid phase. FIG. 3E shows an example of an appearance of the reagent kit. In the Figure, 11 shows a first container containing the tagged cholesterol. 22 shows a second container containing the capture body bound to the enzyme as the label. 33 shows a third container containing the chemiluminescent substrate for the enzyme. 66 shows a solid phase (96-well microplate) for fixing an antibody which binds to a lipoprotein.

Figure 3F:
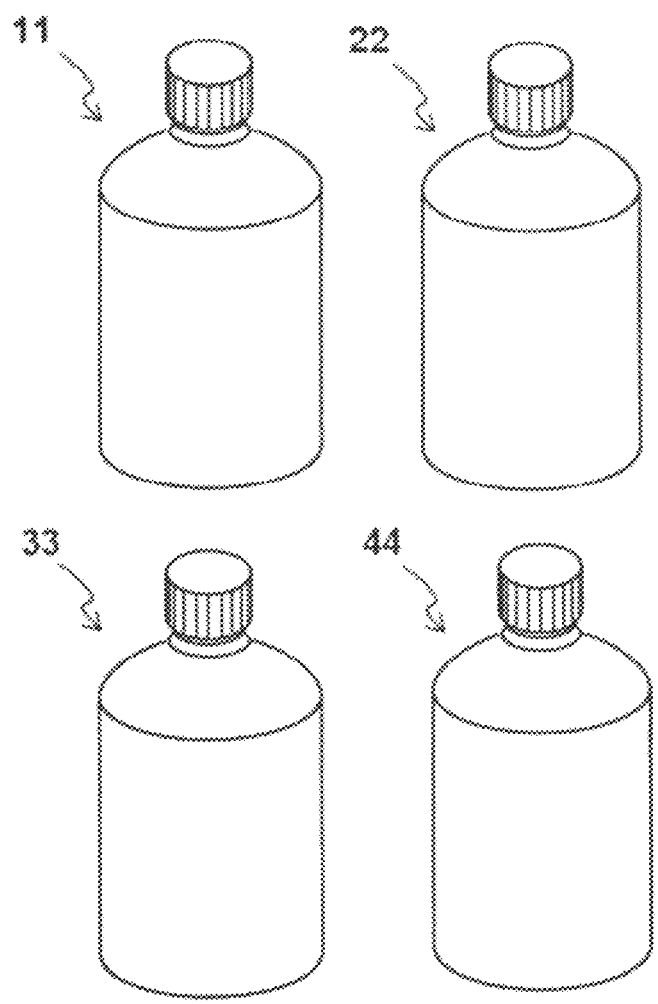
FIG. 3F is a figure showing an example of an appearance of the reagent kit according to the present embodiment.

FIG. 3F shows an example of an appearance of the reagent kit using particles as the solid phase. In the Figure, a first container containing the tagged cholesterol is shown. 22 shows a second container containing the capture body which binds to the enzyme as the label. 33 shows a third container containing a particle for fixing an antibody which binds to a lipoprotein. 44 shows a fourth container containing the chemiluminescent substrate for the enzyme.

The reagent kit may optionally further contain an aqueous medium for diluting the sample, a blocking agent, a fatty acid and a composition containing thereof for the esterification of cholesterol, an oxidant, and the like as a separate reagent. The details of them are similar to description about the measuring method of the present embodiment.

The containers and solid phases containing reagents as described above can be packaged in a box for providing users. The box may include all the reagents and the solid phases, or a part thereof only. The box may further have a pack insert which describes how to use the reagent, and the like.

The use of various reagent as described above for producing the reagent kit for measuring the cholesterol uptake capacity of lipoproteins is also encompassed in the scope of the present invention. That is, the present invention also relates to the use of the tagged cholesterol, the antibody which specifically binds to the lipoprotein (anti-lipoprotein antibody), capture body which specifically binds to the tag, and the label for producing the reagent kit for measuring the cholesterol uptake capacity of lipoproteins. When the label is an enzyme, a substrate for the enzyme may be further used. The solid phase may be further used. The anti-lipoprotein antibody may be fixed on the solid phase.

The tagged cholesterol is encompassed in the scope of the present invention. That is, the tagged cholesterol represented by the following formula (III) is provided:

[Chemical Formula 11]

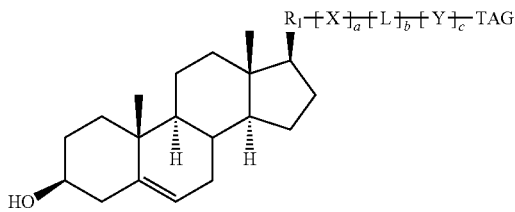

(III)

wherein $R_1$ is an alkylene group having 1 to 6 carbon atoms, which may have a methyl group, X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—, wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;

L represents —$(CH_2)_d$—$[R_3$—$(CH_2)_e]_f$— or —$[(CH_2)_e$—$R_3]_f$—$(CH_2)_d$—, wherein $R_3$ is an oxygen atom, a sulfur atom, —NH—, —NH—(C=O)—, or —(C=O)—NH—;

TAG is a tag;

a and c are identical or different and each represents an integer of 0 to 6;

b is 0 or 1;

d and e are identical or different and each represents an integer of 0 to 12; and f is an integer of 0 to 24.

The tagged cholesterol is suitable for use in the measuring method of the present embodiment. The detail of the tagged cholesterol represented by the formula (III) is similar to description about the measuring method of the present embodiment.

Although the present invention will be described in the EXAMPLES in detail, the present invention is not limited to the EXAMPLES.

EXAMPLES

Example 1

In EXAMPLE 1, whether the cholesterol uptake capacity of HDL can be measured or not was studied by forming a complex of a tagged cholesterol incorporated into HDL and an antibody for capturing HDL on a solid phase and detecting the tag of the tagged cholesterol incorporated into HDL.

(1.1) Extraction of HDL Fraction

The serum (0.1 ml) from healthy persons (n=3) was mixed with the equal amount of 22% polyethylene glycol 4000 (Wako Pure Chemical Industries, Ltd.) to obtain a suspension. After the suspension was left at room temperature for 20 minutes, and centrifuged at 3000 rpm, at room temperature for 15 minutes. Each supernatant was collected as the HDL fraction. The HDL fractions obtained from the serum of three healthy persons were mixed, the resulting mixture (hereinafter, also referred to as "normal specimen") was stored at 4° C. The serum of dyslipidemia patients (n=4) was also treated in the same way to collect the HDL fractions. The HDL fractions obtained from the serum of four patients were mixed, the resulting mixture (hereinafter, also referred to as "abnormal specimen") was stored at 4° C. In EXAMPLE 1, the resulting normal specimen and abnormal specimen were used as biological samples for the following procedure.

(1.2) Formation of Complex of HDL and Anti-ApoAI Antibody on Solid Phase (i) Preparation of Measuring Plate (Fixing of Anti-ApoAI Antibody to Solid Phase)

To each well of 96-well microplate (black plate H for fluorometry, manufactured by Sumitomo Bakelite Co., Ltd.) as the solid phase was added 200 µl of 50 mM Tris-HCl (pH 7.5) and washed. The washing procedure was repeated twice totally. To each well was added 100 µl solution of anti-ApoAI antibody (clone 105, Cat. No. MON05030, SanBio Company Limited) diluted to 10 µl/ml with 50 mM Tris-HCl (pH 7.5), and left at 4° C. longer than overnight. The antibody solution was removed, and 200 µl of PBS was added to each well and washed. The washing procedure was repeated three times totally. To each well was added 200 µl of 2% BSA/PBS, and shaken at 600 rpm, at 25° C. for 2 hours.

(ii) Preparation of Measuring Sample (Contacting HDL with Tagged Cholesterol)

A part of specimen was taken from the normal specimen and abnormal specimen, and each of the ApoAI concentration was measured by using ApoAI measuring kit (N-Assay TIA ApoAI-H, NITTOBO MEDICAL Co., LTD.). The ApoAI concentrations were 883 µg/ml for the normal specimen and 691 µg/ml for the abnormal specimen. The specific procedure for measuring the concentration was performed according to the attached manual to the kit. After the measurement, the normal specimen and abnormal specimen were diluted with a reaction buffer (PBS containing 2% BSA and 2 mM liposome (manufactured by NIPPON FINE CHEMICAL Co., LTD.) to prepare diluted liquids containing HDL fraction having an ApoAI concentration of 0.05, 0.1, or 0.3 µg/ml. As a reference specimen without HDL fraction (ApoAI concentration is 0 µg/ml), the reaction buffer was used. The composition of the liposome contained in the reaction buffer is 2 mM dimyristoyl phosphatidyl glycerol (DMPG), 2 mM cholesterol and 4 mM hydrogenated soybean phosphatidylcoline (HSPC). PBS was prepared by dissolving a phosphate buffered saline tablet (Sigma-Aldrich) with water.

To the reaction buffer was added 0.5 mM BODIPY-tagged cholesterol (TopFluor Cholesterol, Avanti Polar Lipids, Inc.) until the final concentration was 5 µm. After that, the diluted liquids containing HDL fraction was added in a ratio of 1/100 based on the total amount. The resulting mixture was shaken at 800 rpm, at 37° C. for 2 hours. To the resulting mixed liquid were added oxidants (8.8 M hydrogen peroxide, 1.76 mM sodium nitrite and 0.86 mM diethylenetriamine pentaacetic acid (DTPA)). The final concentration of each component after adding oxidants are 1M for hydrogen peroxide, 200 µm for sodium nitrite, and 100 µm for DTPA. The solution was shaken at 800 rpm, at 37° C. for 1 hour to obtain a measuring sample containing HDL in which BODIPY-tagged cholesterol was incorporated.

(iii) Formation of Complex of HDL in which Cholesterol is Incorporated and Anti-ApoAI Antibody BSA solution was removed from the plate in which the anti-ApoAI antibody was fixed, and 100 µl solution of each measuring sample was added to each well. The plate was shaken at 600 rpm, at 25° C. for 1 hour to form a complex of HDL and the anti-ApoAI antibody. In the EXAMPLE 1, two plates capturing the complex were prepared.

(1.3) Measurement of the Amount of the Captured Complex and Confirmation of the Incorporation of Cholesterol by HDL In one of the two plates prepared in (1.2), 100 µl of 10 mM cyclodextrin/PBS was added to each well, and the plate was shaken at 600 rpm, at 25° C. for 30 minutes. The fluorescence intensity was measured by a fluorescence plate reader (Infinite® 200 Pro, manufactured by Tecan Group Ltd.) (excitation at 485 nm/emission at 535 nm). The cyclodextrin solution was removed from the plate after the measurement, and each well was washed with PBS three times. A goat anti-ApoAI serum of a kit for measuring ApoAI (N-Assay TIA ApoAI-H, NITTOBO MEDICAL Co., LTD.) was diluted with a blocking buffer (StartingBlock, Thermo Scientific) at a ratio of 1:1000, and 100 µl of the resulting diluted liquid was added to each well. After the plate was shaken at 600 rpm, at 25° C. for 1 hour, the diluted liquid was removed, and each well was washed with PBS three times. A HRP labeled rabbit anti-goat IgG polyclonal antibody (P0449, Dako) was diluted with a blocking buffer (StartingBlock, Thermo Scientific) at a ratio of 1:1000, and 100 µl of the resulting diluted liquid was added to each well. After the plate was shaken at 600 rpm, at 25° C. for 1 hour, the diluted liquid was removed, and each well was washed with PBS five times. To each well was added 100 µl of a chemiluminescent substrate solution (SuperSignal ELISA Pico, 37069, Thermo Scientific). After the plate was shaken at 600 rpm, at 25° C. for 2 minutes, the amount of luminescence was measured by a microplate reader (Infinite® F200 Pro, manufactured by Tecan Group Ltd.).

(1.4) Measurement of the Amount of Cholesterol Incorporated into HDL by Chemiluminescent The other of the two plates prepared in the (1.2) was washed with PBS five times. A rabbit anti-BODIPY antibody (BODIPY FL Rabbit IgG Fraction, A-5770, Life technologies) was diluted with PBS at a ratio of 1:100, and 100 μl of the resulting diluted liquid was added to each well. After the plate was shaken at 600 rpm, at 25° C. for 1 hour, the diluted liquid was removed, and each well was washed with PBS five times. A HRP labeled goat anti-rabbit IgG polyclonal antibody (P0448, Dako) was diluted with a blocking buffer (StartingBlock, Thermo Scientific) at a ratio of 1:1000, and 100 μl of the resulting diluted liquid was added to each well. After the plate was shaken at 600 rpm, at 25° C. for 1 hour, the diluted liquid was removed, and each well was washed with PBS five times. To each well was added 100 μl of a chemiluminescent substrate solution (SuperSignal ELISA Pico, 37069, Thermo Scientific). After the plate was shaken at 600 rpm, at 25° C. for 2 minutes, the amount of luminescence was measured by a microplate reader (Infinite® F200 Pro, manufactured by Tecan Group Ltd.).

(1.5) Measuring Result and Discussion

The result of sandwich ELISA method in (1.3) is shown in FIG. 1. As shown in FIG. 1, the amount of the complex captured on the plate in which the anti-ApoAI antibody was fixed was increased depending on the ApoAI concentration in the measuring sample. There was no significant difference of the amount of the captured complex between the normal specimen and the abnormal specimen. The fluorescence intensity generated from BODIPY in the captured complex was increased depending on the amount of the captured complex (not shown). Therefore, the incorporation of the BODIPY-tagged cholesterol into HDL was confirmed. The amount of cholesterol incorporated into HDL in the normal specimen was two times higher than that in the abnormal specimen.

Figure 2:
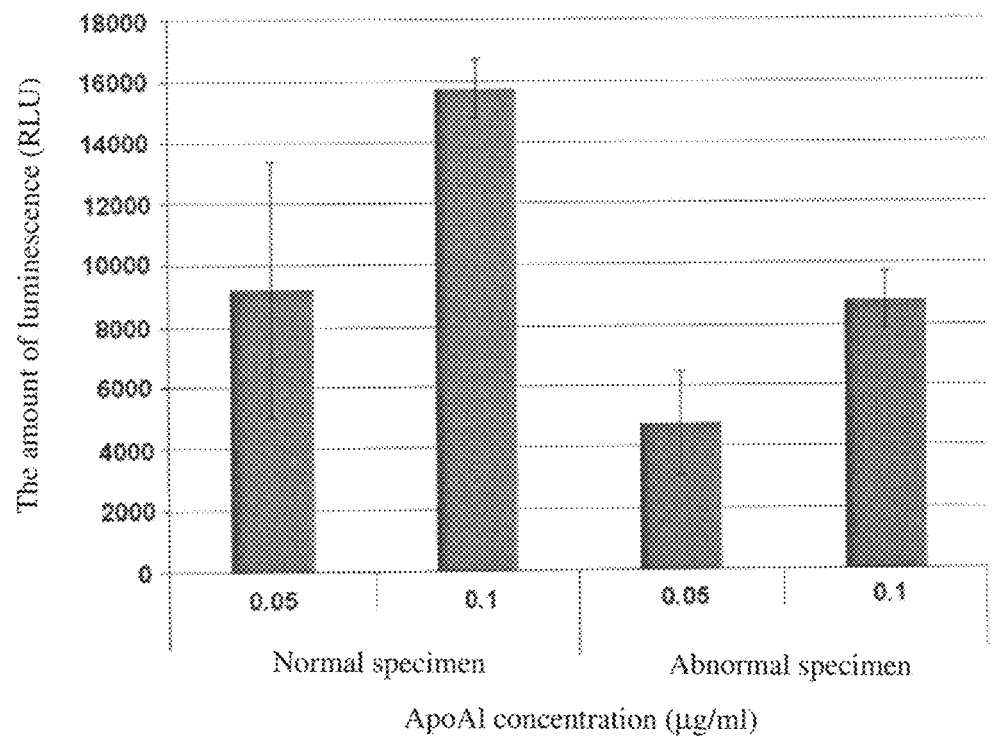
FIG. 2 is a graph showing the amount of the tagged cholesterol incorporated in HDL in the complex captured by an anti-ApoAI antibody, as measured by sandwich ELISA method.

The result in sandwich ELISA method as described in (1.4) is shown in FIG. 2. The graph in FIG. 2 shows a value obtained by subtracting the average of the amount of luminescence of the reference specimen (background) from the average of the amount of luminescence of the diluted liquid containing HDL fraction derived from the normal specimen and the abnormal specimen. As shown in FIG. 2, the measured amount of luminescence was increased depending on the amount of the captured complex. Also, the amount of cholesterol incorporated into HDL in the normal specimen was two times higher than that in the abnormal specimen. The result is similar to the measuring result of the fluorescent generated from BODIPY-added cholesterol incorporated into HDL. The data shows that the cholesterol uptake capacity of HDL can be measured by incorporating the tagged cholesterol into HDL and detecting the tag exposed on the outer surface of HDL.

Example 2

In EXAMPLE 2, cholesterol in which biotin is added via PEG as the linker was prepared. The synthesis scheme of the biotin-tagged cholesterol is shown as follows.

[Chemical Formula 12]

(First step)

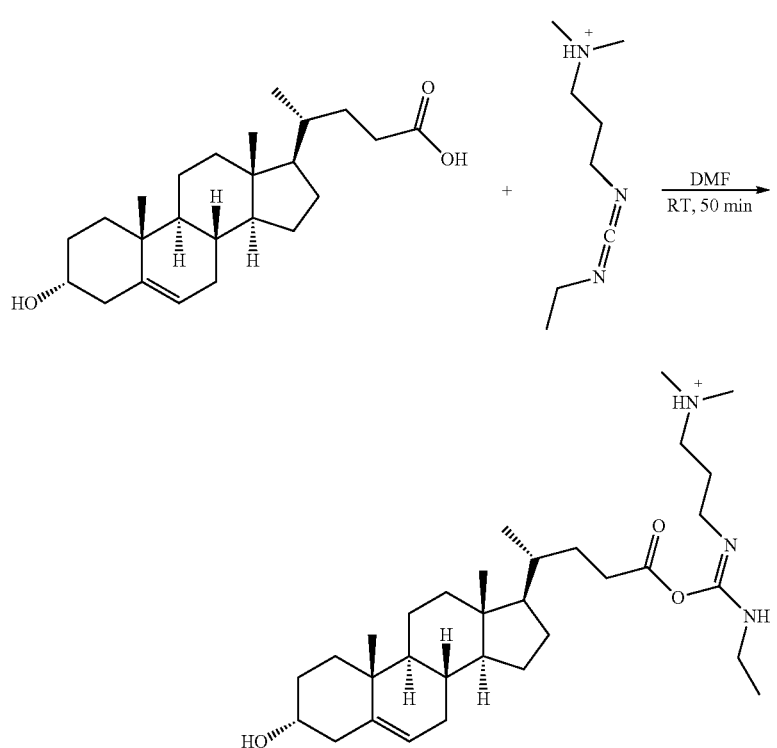

(Second step)

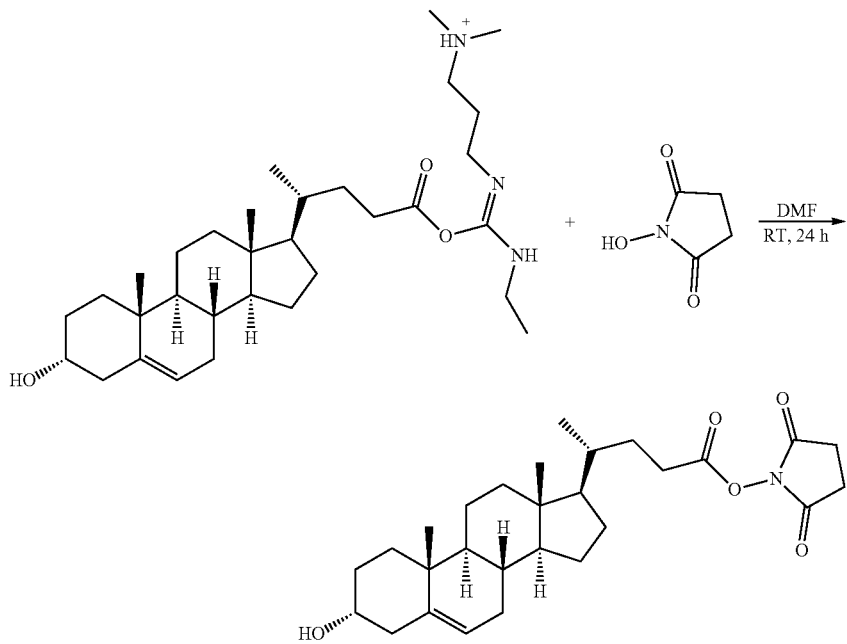

(Third step)

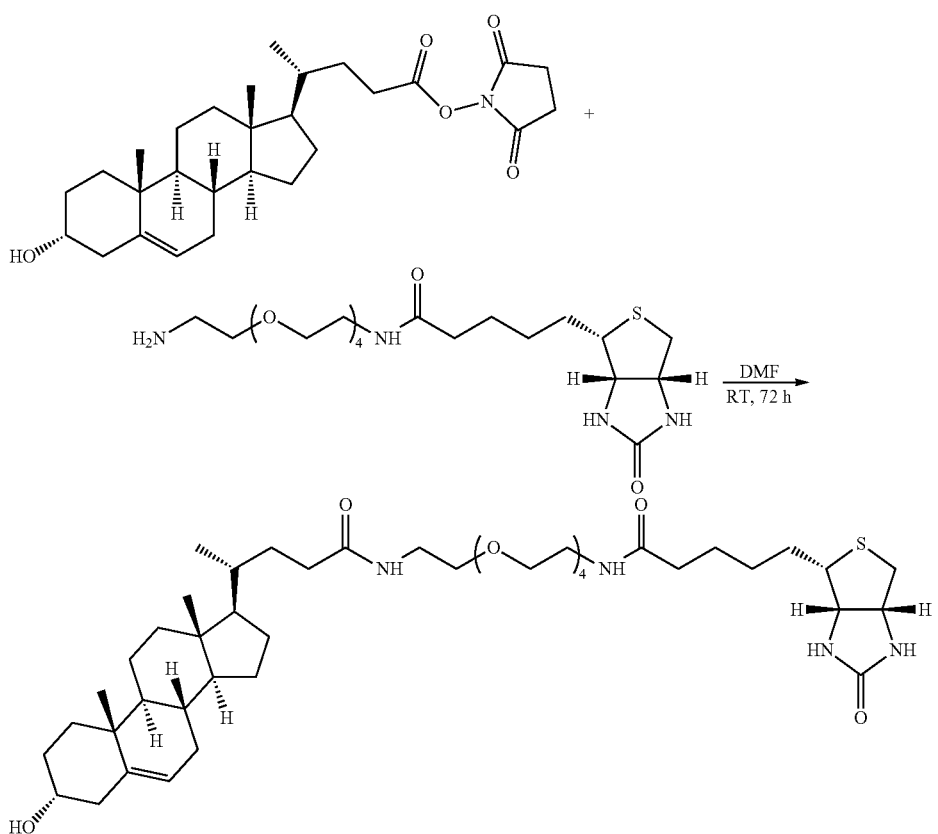

A solution of 0.05 mmol of 3β-hydroxy-Δ5-cholenoic acid (Tokyo Chemical Industry Co., Ltd.) and 0.075 mmol of aqueous carbodiimide(1-ethyl-3-(3-dimethylaminopropyl)carbodiimide hydrochloride, DOJINDO LABORATORIES) in 0.5 ml of N,N-dimethylformamide (hereinafter, also referred to "DMF", Wako Pure Chemical Industries, Ltd.) was stirred at room temperature under Ar atmosphere for 50 minutes (first step). To the resulting reaction liquid was added a solution of 0.075 mmol of N-hydroxysuccinimide (Sigma) in 100 μl of DMF, and stirred at room temperature under Ar atmosphere for 24 hours (second step). A solution of the starting material (3β-hydroxy-Δ5-cholenoic acid), the reaction liquid obtained in the first step, and the reaction liquid obtained in the second step were individually spotted on a silica gel plate, and the plate was developed with a developing solvent (hexane:tetrahydrofuran (THF)=5:5). The Rf value of the starting material was 0.6, that of the product in the first step was 0.55, and that of the product in the second step was 0.5.

To the reaction liquid obtained in the second step was added a solution of 0.075 mmol of Biotin-PEG4-Amine (Biovision) in 100 µl of DMF, and stirred at room temperature under Ar atmosphere for 72 hours or more (third step). The reaction liquid obtained in the second step, the reaction liquid obtained in the third step, and mixed liquid thereof were individually spotted on a silica gel plate, and the plate was developed with a developing solvent (chloroform:methanol:THF=9:1:1). The Rf value of the product in the third step (biotin-tagged cholesterol) was 0.3. The biotin-tagged cholesterol was collected by a thin layer chromatography.

Example 3

The BODIPY-added cholesterol in EXAMPLE 1 and the biotin-added cholesterol in EXAMPLE 2 were used to measure the cholesterol uptake capacity of HDL, and observed the effect of the linker on the tagged cholesterol.
(3.1) Sample The abnormal specimen prepared in EXAMPLE 1 was used as the sample containing HDL fraction.
(3.2) Formation of Complex of HDL and Anti-ApoAI Antibody on Solid Phase (i) Preparation of Measuring Plate The anti-ApoAI antibody was fixed on 96-well microplate as similar to EXAMPLE 1 to prepare a measuring plate.

(ii) Preparation of Measuring Sample

The abnormal specimen was diluted with a reaction buffer (PBS) to prepare diluted liquids containing HDL fraction having an ApoAI concentration of 0.1 µg/ml. As a reference specimen without HDL fraction (ApoAI concentration is 0 µg/ml), the reaction buffer was used. PBS was prepared by dissolving a phosphate buffered saline tablet (Sigma-Aldrich) with water. To the reaction buffer was added 0.5 mM biotin-tagged cholesterol until the final concentration was 5 µm. After that, the diluted liquids containing HDL fraction was added in a ratio of 1/100 based on the total amount. The resulting mixture was shaken at 800 rpm, at 37° C. for 2 hours to obtain a measuring sample containing HDL in which biotin-tagged cholesterol was incorporated.

Figure 4:
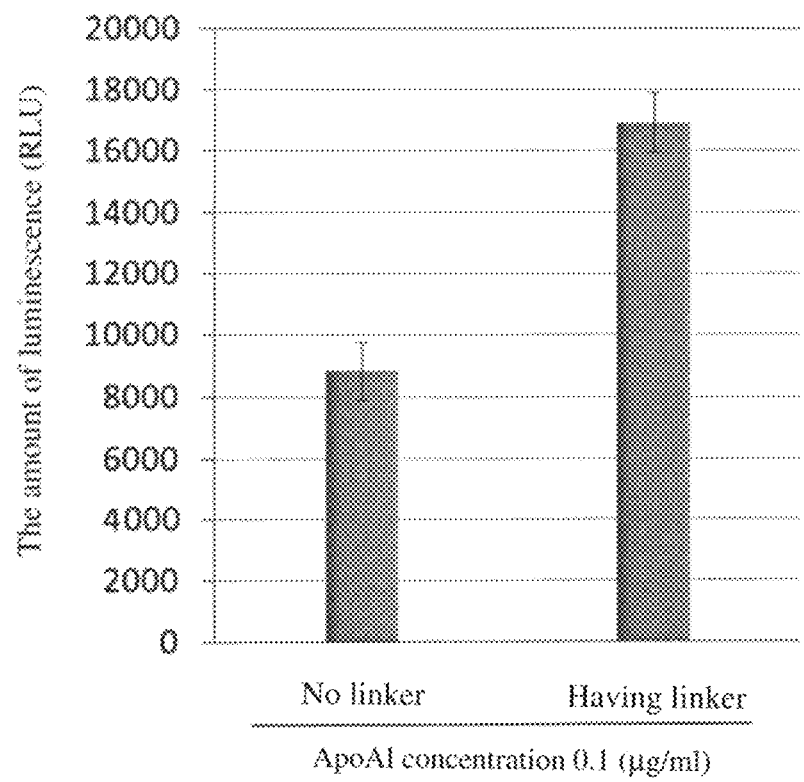
FIG. 4 is a graph showing the amount of the tagged cholesterol incorporated in HDL in the complex captured by an anti-ApoAI antibody, as measured by sandwich ELISA method.

(iii) Formation of Complex of HDL in which Cholesterol is Incorporated and Anti-ApoAI Antibody BSA solution was removed from the plate in which the anti-ApoAI antibody was fixed, and 200 µl solution of PBS was added to each well. The washing procedure was performed three times totally. To each well was added 100 µl solution of each measuring sample. The plate was shaken at 600 rpm, at 25° C. for 1 hour to form a complex of HDL and the anti-ApoAI antibody. In the EXAMPLE 3, one plate capturing the complex was prepared.
(3.3) Measurement of the Amount of Cholesterol Incorporated into HDL by Chemiluminescent The plate prepared in the (3.2) was washed with PBS five times. HRP labeled streptavidin (N100, Life technologies) was diluted with a blocking buffer (StartingBlock, Thermo Scientific) at a ratio of 1:3000, and 100 µl of the resulting diluted liquid was added to each well. After the plate was shaken at 600 rpm, at 25° C. for 1 hour, the diluted liquid was removed, and each well was washed with PBS five times. To each well was added 100 µl of a chemiluminescent substrate solution (SuperSignal ELISA Pico, 37069, Thermo Scientific). After the plate was shaken at 600 rpm, at 25° C. for 2 minutes, the amount of luminescence was measured by a microplate reader (Infinite® F200 Pro, manufactured by Tecan Group Ltd.).
(3.4) Measurement of the Amount of the Captured Complex After the measurement in (3.3), 200 µl of PBS was added to each well and washed. The washing procedure was performed three times totally. A goat anti-ApoAI serum of a kit for measuring ApoAI (N-Assay TIA ApoAI-H, NITTOBO MEDICAL Co., LTD.) was diluted with a blocking buffer (StartingBlock, Thermo Scientific) at a ratio of 1:1000, and 100 µl of the resulting diluted liquid was added to each well. After the plate was shaken at 600 rpm, at 25° C. for 1 hour, the diluted liquid was removed, and each well was washed with PBS three times. A HRP labeled rabbit anti-goat IgG polyclonal antibody (P0449, Dako) was diluted with a blocking buffer (StartingBlock, Thermo Scientific) at a ratio of 1:1000, and 100 µl of the resulting diluted liquid was added to each well. After the plate was shaken at 600 rpm, at 25° C. for 1 hour, the diluted liquid was removed, and each well was washed with PBS five times. To each well was added 100 µl of a chemiluminescent substrate solution (SuperSignal ELISA Pico, 37069, Thermo Scientific). After the plate was shaken at 600 rpm, at 25° C. for 2 minutes, the amount of luminescence was measured by a microplate reader (Infinite® F200 Pro, manufactured by Tecan Group Ltd.).
(3.5) Measuring Result The measuring result in (3.4) could confirm that the formation of the complex of HDL and the anti-ApoAI antibody on the plate (not shown). The measuring result in (3.3) is shown in Table 1 and FIG. 4. In Table 1 and FIG. 4, the data relating to the amount of BODIPY-tagged cholesterol incorporated into HDL in the diluted liquid containing HDL fraction derived from the abnormal specimen in EXAMPLE 1 (ApoAI concentration is 0.1 µg/ml) and the reference specimen are arranged for the comparison. Table 1 shows the average of the amount of luminescence (RLU) and SD of the diluted liquid containing HDL fraction derived from the abnormal specimen and the reference specimen. The graph in FIG. 4 shows a value obtained by subtracting the average of the amount of luminescence of the reference specimen (background) from the average of the amount of luminescence of the diluted liquid containing HDL fraction derived from the abnormal specimen. In FIG. 1, "BODIPY" refers to BODIPY-tagged cholesterol, "PEG4-Biotin" refers to the biotin-tagged cholesterol prepared in EXAMPLE 2, and "abnormal specimen" refers to the diluted liquid containing HDL fraction derived from the abnormal specimen (ApoAI concentration is 0.1 µg/ml). In FIG. 4, "no linker" shows BODIPY-tagged cholesterol, and "having linker" shows a biotin-tagged cholesterol.

TABLE 1

| | Reference antibody | | Abnormal specimen | |
|---|---|---|---|---|
| Tagged cholesterol | The average | SD | The average | SD |
| BODIPY | 36460 | 1578 | 45271 | 920 |
| PEG4-Biotin | 1970 | 348 | 18880 | 985 |

As shown in Table 1 and FIG. 4, the use of the biotin-tagged cholesterol having the linker provided higher amount of luminescence than background. Therefore, in the measuring method of the present embodiment, it was shown that the use of the biotin-tagged cholesterol having the linker allows to measure the cholesterol uptake capacity of lipoproteins similar to BODIPY-added cholesterol.

Example 4

Various cholesterol having biotin added via various length of PEG linker were prepared. These biotin-tagged cholesterol and BODYPI-tagged cholesterol in EXAMPLE 1 are used to measure the cholesterol uptake capacity of HDL.
(4.1) Preparation of Biotin-Tagged Cholesterol
In the third step of EXAMPLE 2, various biotin-tagged cholesterol having biotin added via various length of PEG linker were prepared in similar method as in EXAMPLE 2, except that 0.075 mmol of EZ-Link™ Amine-PEG2-Biotin (Life technologies), Biotin-PEG7-amine (BroadPharm), O-(2-aminoethyl)-O'-[2-(biotinylamino)ethyl]octaethylene glycol (Sigma Ardrich), or EZ-Link™ Amine-PEG11-Biotin (Life technologies) was used instead of Biotin-PEG4-Amine. The resulting biotin-tagged cholesterol corresponds to the tagged cholesterol in the above formula (V) wherein n is 2, 7, 9, or 11.

According to the following synthetic scheme, the biotin-tagged cholesterol in the above formula (V) wherein n is 3 was prepared. Specifically, 4.2 μmol of 24-amino-5-colen-3β-ol (synthesized by NARD INSTITUTE, LTD. on commission) and 5.0 μmol of Biotin-PEG3-NHS ester (BPS Bioscience) were dissolved in 100 μl of DMSO (Wako Pure Chemical Industries, Ltd.), and stirred at room temperature under Ar atmosphere for 72 hours. The resulting reaction liquid was spotted on a silica gel plate, and the biotin-tagged cholesterol was collected by a thin layer chromatography.

[Chemical Formula 13]

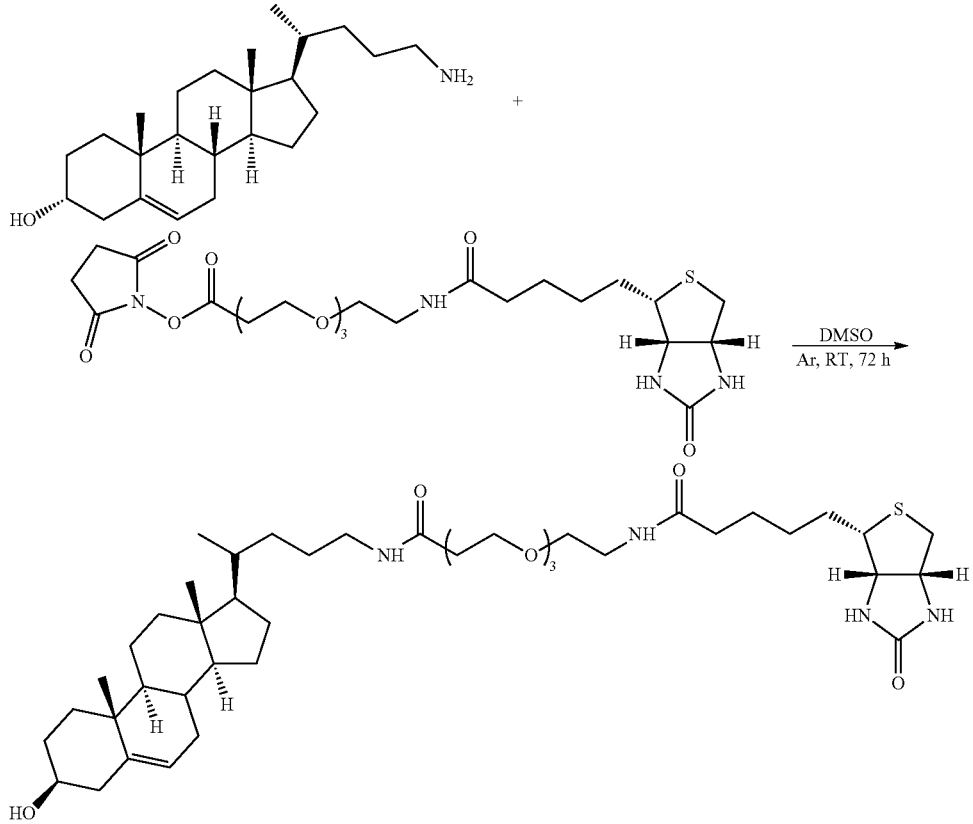

In EXAMPLE 4, these biotin-tagged cholesterols are also referred to as PEG2-Biotin, PEG3-Biotin, PEG4-Biotin, PEG7-Biotin, PEG9-Biotin and PEG11-Biotin depending on the length of PEG linker. Each Rf value of the biotin-tagged cholesterols and a developing solvent used for the thin layer chromatography are shown in Table 2.

TABLE 2

| Biotin-tagged cholesterol | Developing solvent | Rf value |
| --- | --- | --- |
| PEG2-Biotin | Chloroform:methanol = 8:2 | 0.7 |
| PEG3-Biotin | Chloroform:methanol:THF = 9:2:1 | 0.45 |
| PEG4-Biotin | Chloroform:methanol:THF = 9:1:1 | 0.3 |
| PEG7-Biotin | Chloroform:methanol:THF = 9:1:1 | 0.25 |
| PEG9-Biotin | Chloroform:methanol:THF = 6:2:4 | 0.25 |
| PEG11-Biotin | Chloroform:methanol:THF = 9:1:1 | 0.2 |

(4.2) Sample
The abnormal specimen prepared in EXAMPLE 1 was used as the sample containing HDL fraction.
(4.3) Formation of Complex of HDL and Anti-ApoAI Antibody on Solid Phase
 (i) Preparation of Measuring Plate
The anti-ApoAI antibody was fixed on 96-well microplate similar to EXAMPLE 1 to prepare a measuring plate.
 (ii) Preparation of Measuring Sample
BODIPY-tagged cholesterol was used to prepare a measuring sample from the abnormal specimen similar to EXAMPLE 1. Each PEG2-Biotin, PEG3-Biotin, PEG4-Biotin, PEG7-Biotin, PEG9-Biotin and PEG11-Biotin was used to prepare a measuring sample from the abnormal specimen similar to EXAMPLE 3.

(iii) Formation of Complex of HDL in which Cholesterol is Incorporated and Anti-ApoAI Antibody The complex of HDL and the anti-ApoAI antibody were formed on the plate similar to EXAMPLE 3. In the EXAMPLE 4, one plate capturing the complex was prepared.

(4.4) Measurement of the Amount of Cholesterol Incorporated into HDL and the Captured Complex For BODIPY-tagged cholesterol, the amount of cholesterol incorporated into HDL was measured by using a rabbit anti-BODIPY antibody and a HRP labeled goat anti-rabbit IgG polyclonal antibody by chemiluminescent similar to EXAMPLE 1. For the biotin-tagged cholesterol, the amount of cholesterol incorporated into HDL was measured by using a HRP labeled streptavidin by chemiluminescent similar to EXAMPLE 3. The amount of the captured complex were measured similar to EXAMPLE 3.

(4.5) Measuring Result

From the measuring result of the amount of the captured complex, it could be confirmed that the complex of HDL and the anti-ApoAI antibody were formed on the plate. The measuring result of the amount of cholesterol incorporated in HDL is shown in Table 3. Table 3 shows the average of the amount of luminescence (RLU) and SD of the diluted liquid containing HDL fraction derived from the abnormal specimen and the reference specimen. In FIG. 3, "BODIPY" refers to BODIPY-tagged cholesterol, and "abnormal specimen" refers to the diluted liquid containing HDL fraction derived from the abnormal specimen (ApoAI concentration is 0.1 µg/ml).

TABLE 3

| Tagged cholesterol | Reference antibody | | Abnormal specimen | |
|---|---|---|---|---|
| | The average | SD | The average | SD |
| BODIPY | 19649 | 986 | 25603 | 613 |
| PEG2-Biotin | 3501 | 400 | 6409 | 1229 |
| PEG3-Biotin | 4461 | 435 | 6880 | 1131 |
| PEG4-Biotin | 1970 | 348 | 18880 | 985 |
| PEG7-Biotin | 8368 | 1227 | 50084 | 4168 |
| PEG9-Biotin | 2710 | 211 | 4805 | 461 |
| PEG11-Biotin | 7377 | 1225 | 18957 | 782 |

As shown in Table 3, the use of all biotin-tagged cholesterols having the PEG linker provided higher amount of luminescence than background. Therefore, in the measuring method of the present embodiment, it was shown that the use of the biotin-tagged cholesterol having the various length of the linker allows to measure the cholesterol uptake capacity of lipoproteins similar to BODIPY-tagged cholesterol.

Example 5

In EXAMPLE 5, cholesterol in which DNP was added as the tag was prepared. The DNP-tagged cholesterol and the BODIPY-tagged cholesterol in EXAMPLE 1 were used to measure the cholesterol uptake capacity of HDL. The measurement was performed in ELISA method using a magnetic particle as the solid phase.

(5.1) Preparation of DNP-tagged Cholesterol

Similar to the first step of EXAMPLE 2, 3β-hydroxy-Δ5-cholenoic acid and a water-soluble carbodiimide were dissolved in DMF, and reacted at room temperature under Ar atmosphere. Similar to the second step of EXAMPLE 2, to the reaction liquid obtained in the first step was added a solution of N-hydroxysuccinimide in DMF, and reacted at room temperature under Ar atmosphere. The reaction liquid obtained in the first step, and the reaction liquid obtained in the second step were individually spotted on a silica gel plate, and the plate was developed with a developing solvent (hexane:ethyl acetate=4:6). The Rf value of the product in the first step was 0.45, and that of the product in the second step was 0.5.

In the third step of EXAMPLE 2, DNP-tagged cholesterol were prepared in similar method as in EXAMPLE 2, except that N1-(2,4-dinitrophenyl)ethane-1,2-diamine (Combi-Blocks) was used instead of Biotin-PEG4-Amine. The third step in the synthesis scheme of the DNP-tagged cholesterol is as follows.

[Chemical Formula 14]

(Third step)

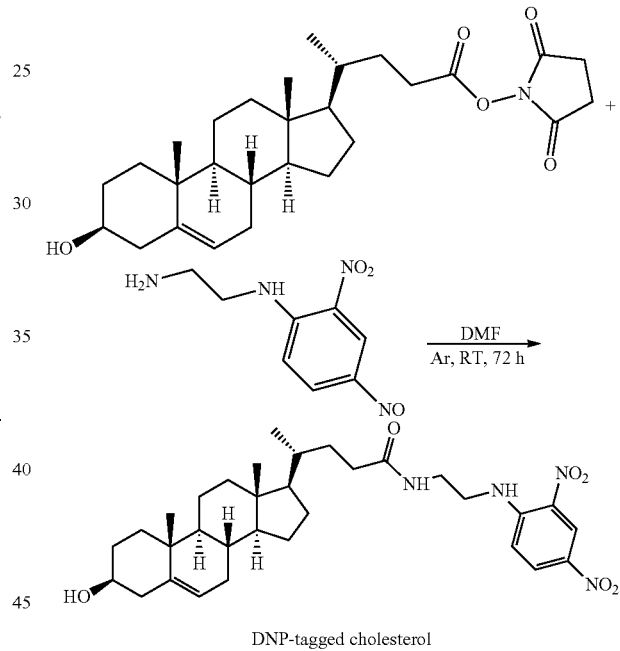

DNP-tagged cholesterol

The reaction liquid obtained in the second step, the reaction liquid obtained in the third step, and the mixed liquid thereof were individually spotted on a silica gel plate, and the plate was developed with a developing solvent (hexane:THF=3:7). The Rf value of the product in the third step (DNP-tagged cholesterol) was 0.7. The DNP-tagged cholesterol was collected by a thin layer chromatography.

(5.2) Analysis of DNP-Tagged Cholesterol

The collected DNP tagged cholesterol was separated and purified by high performance liquid chromatography (HPLC). The resulting purified substance was analyzed by nuclear magnetic resonance (NMR) and liquid chromatography-mass spectrometry (LC-MS). $^1$H-NMR spectrum was measured at 400 MHz, and $^{13}$C-NMR spectrum was measured at 100 MHz by using JNM-ECX400P (manufactured by JEOL Ltd.). The conditions for measuring HPLC and LC-MS are as follows. The purification by HPLC and the analysis by NMR and LC-MS were performed by NARD INSTITUTE, LTD. on commission.

(HPLC)
Instrument: LC-2010 (manufactured by SHIMADZU CORPORATION)
Column: Kinetex® 5 µm EVO C18 100A 4.6×150 mm (manufactured by SHIMADZU GLC Ltd.)
Column Temperature: 40° C.
Flow Rate: 1 mL/min
Mobile Phase A: 1 mM phosphate buffer (pH 7.4)
Mobile Phase B: acetonitrile (MeCN)

TABLE 4

| Gradient condition | | |
|---|---|---|
| Time (min) | Mobile phase A (%) | Mobile phase B (%) |
| 0.00 | 90.0 | 10.0 |
| 7.00 | 0.00 | 100 |
| 15.0 | 0.00 | 100 |
| 20.0 | 90.0 | 10.0 |

(LC-MS)
Instruments
MS detector: waters 3100 Mass Detector (Manufactured by Waters Corporation)
FAD detector: waters 2996 Photodiode Array Detector (Manufactured by Waters Corporation)
ELSD: waters 2424 ELS Detector (Manufactured by Waters Corporation)
Pump: waters 2545 Binary Gradient Module (Manufactured by Waters Corporation)
SFO: waters SFO System Fluidics Organizer (Manufactured by Waters Corporation)
Column: Atlantis® 3.5 µm 4.6×50 mm (Manufactured by Waters Corporation)
Column Temperature: room temperature
Flow Rate: 2 mL/min
Mobile Phase A: 0.1% aqueous trifluoroacetic acid (TFA) solution
Mobile Phase B: MeCN

TABLE 5

| Gradient condition | | |
|---|---|---|
| Time (min) | Mobile phase A (%) | Mobile phase B (%) |
| 0.00 | 95.0 | 5.00 |
| 0.50 | 95.0 | 5.00 |
| 3.00 | 5.00 | 95.0 |
| 5.00 | 5.00 | 95.0 |

Ionization Method: ESI (electrospray ionization) method
Mass Voltage: 30 V
Positive mode
The measuring results of NMR and LC-MS are shown as follows. These results showed that DNP-tagged cholesterol represented by the formula (VI) was obtained.
LC-MS m/z 583.7 [M+H]$^+$
$^1$H-NMR (CDCl$_3$) δ: 9.14 (1H, d, J=2.3 Hz), 8.74 (1H, s), 8.30 (1H, dd, J=9.4, 2.5 Hz), 7.11 (1H, d, J=9.6 Hz), 5.83-5.72 (1H, br m), 5.35 (1H, d, J=5.0 Hz), 3.66-3.47 (5H, m), 2.29-2.23 (3H, m), 2.15-2.07 (1H, m), 2.00-1.94 (2H, m), 1.89-1.75 (4H, m), 1.53-1.23 (10H, m), 1.19-0.88 (12H, m), 0.66 (3H, s).
$^{13}$C-NMR (CDCl$_3$) δ: 174.8 (C), 148.4 (C), 140.7 (C), 136.4 (C), 133.7 (C), 130.5 (CH), 124.3 (CH), 121.6 (CH), 114.0 (CH), 71.8 (CH), 56.7 (CH), 55.7 (CH), 50.0 (CH), 43.0 (CH$_2$), 42.4 (CH$_2$), 42.3 (C), 39.7 (CH$_2$), 38.5 (CH$_2$), 37.2 (CH$_2$), 36.5 (C), 35.5 (CH), 33.4 (CH$_2$), 31.9 (CH), 31.8 (CH$_2$), 31.6 (CH$_2$), 28.2 (CH$_2$), 24.2 (CH$_2$), 22.9 (CH), 21.0 (CH), 19.4 (CH$_3$), 18.4 (CH$_3$), 11.8 (CH$_3$).

(5.3) Formation of Complex of HDL and Anti-ApoAI Antibody on Solid Phase
(i) Preparation of Measuring Sample
The abnormal specimen in EXAMPLE 1 was diluted with a reaction buffer (PBS) to prepare diluted liquids containing HDL fraction having an ApoAI concentration of 0.2 µg/ml. As a reference specimen without HDL fraction (ApoAI concentration is 0 µg/ml), the reaction buffer was used. PBS was prepared by dissolving a phosphate buffered saline tablet (Sigma-Aldrich) with water. To the reaction buffer was added 0.5 mM DNP-tagged cholesterol or 0.5 mM BODIPY-tagged cholesterol (TopFluor Cholesterol, AvantiPolar Lipids) until the final concentration was 5 µm. After that, the diluted liquids containing HDL fraction was added in a ratio of 1/100 based on the total amount. The resulting mixture was shaken at 800 rpm, at 37° C. for 2 hours to obtain a measuring sample.

(ii) Formation of Complex of HDL in which Cholesterol is Incorporated and Anti-ApoAI Antibody
30 µl of the measuring sample was taken, and transferred to another tube. In the tube, 30 µl of 2.5 ng/µl biotinylated ApoAI antibody (obtained by reducing anti-ApoAI antibody (SANBIO) with 2-mercaptoethylamine hydrochloride (NA-CALAI TESUE, INC. and labeling with Biotin-PEACS-maleimide (Dojindo)), was added to the sample solution and reacted at 42° C. for 12 minutes. To the tube was added 30 µl of HISCL magnetic particle (SYSMEX CORPORATION), and reacted at 42° C. for 10 minutes. Since avidin is fixed on the surface of HISCL magnetic particle, the biotinylated anti-ApoAI antibody in the complex bonds to the surface of the magnetic particle. The supernatant was removed by collecting the magnetic particle in the reaction liquid magnetically. HISCL line cleaner (SYSMEX CORPORATION) was added to wash the magnetic particle. The washing procedure was further performed twice. The supernatant was removed by collecting the magnetic particle magnetically.

(5.4) Measurement of the Amount of Cholesterol Incorporated into HDL by Chemiluminescence
(i) Measurement of the Amount of the DNP-Tagged Cholesterol
To the magnetic particle having HDL in which the DNP-tagged cholesterol is incorporated was added 100 µl of 333 ng/µl ALP labeled anti-DNP antibody (obtained by labeling the anti-DNP antibody (produced by KITAYAMA LABES CO., LTD. on commission) with ALP using ALP Labeling Kit-SH (Dojindo)), and reacted at 42° C. for 10 minutes. The supernatant was removed by collecting the magnetic particle in the reaction liquid magnetically. HISCL line cleaner (SYSMEX CORPORATION) was added to wash the magnetic particle. The washing procedure was further performed twice. The magnetic particle was transferred to another tube, and the supernatant was removed by collecting the magnetic particle magnetically. To the tube were added 50 µl of R4 reagent of HISCL luminescence substrate (SYSMEX CORPORATION) and 100 µl of R5 reagent, and reacted at 42° C. for 5 minutes. After the reaction, the magnetic particle was collected magnetically, and the supernatant was transferred to 96-well plate. The amount of luminescence was measured by a microplate reader (Infinite® F200 Pro, manufactured by Tecan Group Ltd.).

(ii) Measurement of the Amount of BODIPY-Tagged Cholesterol

To the magnetic particle having HDL in which the BODIPY-tagged cholesterol is incorporated was added 100 μl of the diluted liquid of a rabbit anti-BODIPY antibody (Life technologies), and reacted at 25° C. for 60 minutes, as similar to EXAMPLE 1. The supernatant was removed by collecting the magnetic particle in the reaction liquid magnetically. HISCL line cleaner (SYSMEX CORPORATION) was added to wash the magnetic particle. The washing procedure was further performed twice. The supernatant was removed by collecting the magnetic particle magnetically. To the magnetic particle was added 100 μl of the diluted liquid of HRP labeled goat anti-rabbit IgG polyclonal antibody (Dako), and reacted at 25° C. for 60 minutes, as similar to EXAMPLE 1. After the reaction, washing the magnetic particle with HISCL line cleaner (SYSMEX CORPORATION) was performed three times. The magnetic particle was transferred to another tube, and the supernatant was removed by collecting the magnetic particle magnetically. To the magnetic particle was added 100 μl of a chemiluminescent substrate solution (SuperSignal ELISA Pico, 37069, Thermo Scientific), and reacted at 25° C. for 2 minutes. After the reaction, the magnetic particle was collected magnetically, and the supernatant was transferred to 96-well plate. The amount of luminescence was measured by a microplate reader (Infinite® F200 Pro, manufactured by Tecan Group Ltd.).

(5.5) Measuring Result

Figure 5:
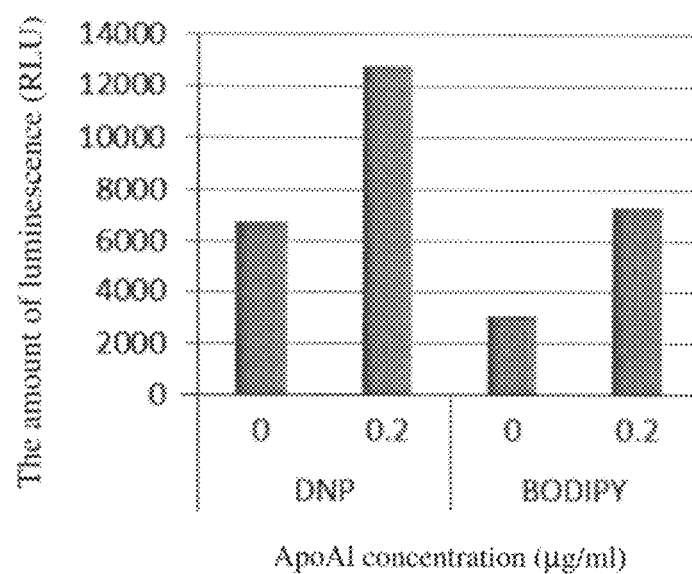
FIG. 5 is a graph showing the amount of the tagged cholesterol incorporated in HDL in the complex captured by an anti-ApoAI antibody, as measured by ELISA method using a magnetic particle.

The measuring result is shown in FIG. 5. As shown in FIG. 5, the use of all BODIPY-tagged cholesterols and DNP-tagged cholesterols provided higher amount of luminescence than background. Therefore, in the measuring method of the present embodiment, it was shown that the use of the DNP-tagged cholesterol allows to measure the cholesterol uptake capacity of lipoproteins similar to BODIPY-tagged cholesterol.

This application relates to Japanese Patent Application Publication No. 2015-110510 filed on May 29, 2015, Japanese Patent Application Publication No. 2015-193648 filed on Sep. 30, 2015, Japanese Patent Application Publication No. 2015-206422 filed on Oct. 20, 2015, and Japanese Patent Application Publication No. 2016-046069 filed on Mar. 9, 2016. All these claims, specifications, figures, and abstracts are incorporated by reference herein.

EXPLANATION OF REFERENCES

11: first container
22: second container
33: third container
44: fourth container
55: fifth container
66: solid phase (96-well microplate)

The invention claimed is:

1. A method for measuring a signal from a complex comprising a cholesterol, comprising the steps of:
   forming the complex by contacting a lipoprotein in a sample, a tagged cholesterol, and an antibody which specifically binds to the lipoprotein, wherein the complex comprises the lipoprotein, the tagged cholesterol and the antibody;
   labeling a tag of the tagged cholesterol in the complex by bonding a label and a capture body with the complex, wherein the capture body specifically binds to the tag; and
   detecting a signal resulted from the label which has been bound to the complex,
   wherein the tagged cholesterol is represented by the following formula (III):

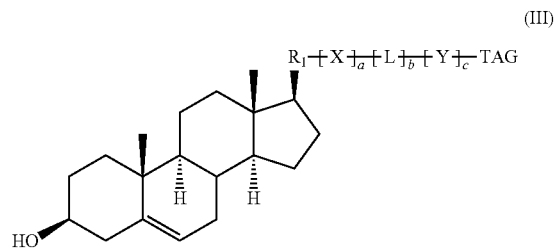

wherein $R_1$ is an alkylene group having 1 to 6 carbon atoms, which may have a methyl group, X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$R_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—, wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;

L represents —$(CH_2)_d$—$[R_3$—$(CH_2)_e]_f$— or —$[(CH_2)_e$—$R_3]_f$—$(CH_2)_d$—, wherein $R_3$ is an oxygen atom, a sulfur atom, —NH—, —NH—(C=O)—, or —(C=O)—NH—;

TAG is a tag;

a and c are identical or different and each represents an integer of 0 to 6;

b is 0 or 1;

d and e are identical or different and each represents an integer of 0 to 12; and f is an integer of 0 to 24.

2. The method according to claim 1, wherein, in the labeling step, a labeled capture body comprising the label and the capture body is bound to the complex.

3. The method according to claim 1, wherein the complex is formed on the solid phase in the forming step.

4. The method according to claim 1, further comprising the B/F separation step for removing an unreacted free component which has not formed the complex after the forming step and before the labeling step.

5. The method according to claim 1, further comprising the B/F separation step for removing an unreacted free component which has not been bound to the complex after the labeling step and before the detecting step.

6. The method according to claim 1, wherein the label is an enzyme, and the signal is a chemiluminescent signal resulted by contacting the enzyme with a substrate for the enzyme.

7. The method according to claim 6, wherein the enzyme is a peroxidase or an alkaline phosphatase.

8. The method according to claim 1, wherein the capture body is: an antibody which specifically binds to the tag; avidin; or streptavidin.

9. The method according to claim 1, wherein the antibody bound to the lipoprotein is an anti-ApoAI antibody.

10. The method according to claim 1, wherein the tagged cholesterol is a cholesterol in which a tag is bound directly or indirectly via a linker at any of C20-C27 positions of the cholesterol.

11. The method according to claim 10, wherein the linker is hydrophilic.

12. The method according to claim 1, wherein the tag has the structure represented by the following formula (I):

[Chemical Formula 2]

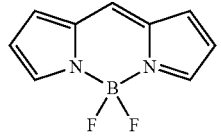
(I)

[Chemical Formula 5]

or the structure represented by the following formula (II):

[Chemical Formula 3]

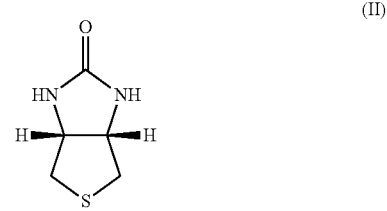
(II)

or 2,4-dinitrophenyl group.

13. The method according to claim 12, wherein the tagged cholesterol is represented by the following formula (IV):

[Chemical Formula 4]

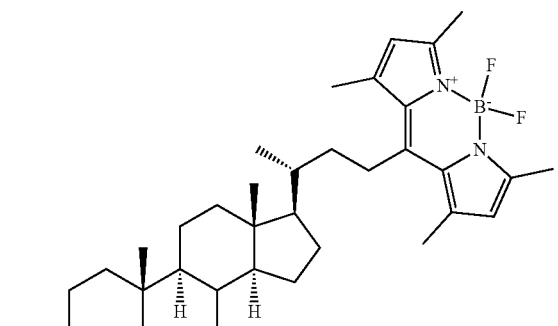
(IV)

or the following formula (V):

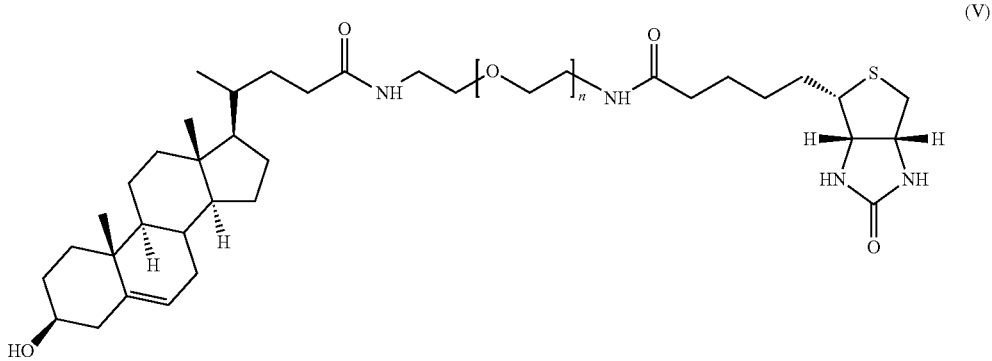
(V)

wherein n is an integer of 0 to 24
or the following formula (VI):

[Chemical Formula 6]

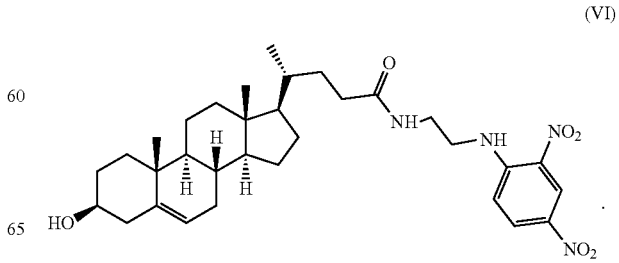
(VI)

14. The method according to claim 1, wherein the sample is blood, serum, or plasma.

15. The method according to claim 1, wherein the lipoprotein is a high-density lipoprotein.

16. The method according to claim 1, wherein the tag is 2,4-dinitrophenyl group and the capture body is an anti-DNP antibody.

17. A method for measuring a signal from a complex comprising a cholesterol, comprising the steps of:
forming the complex by contacting a lipoprotein in a sample, a tagged cholesterol, and an antibody which specifically binds to the lipoprotein, wherein the complex comprises the lipoprotein, the tagged cholesterol and the antibody;
labeling a tag of the tagged cholesterol in the complex by bonding a label and a capture body with the complex, wherein the tag is exposed on the outer surface of the lipoprotein in the complex, and the capture body specifically binds to the tag exposed on the outer surface of the lipoprotein in the complex; and
detecting a signal resulted from the label which has been bound to the complex,
wherein the tagged cholesterol is represented by the following formula (III):

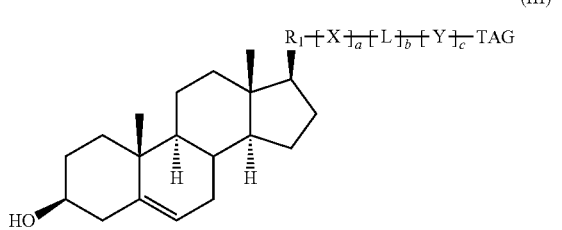

(III)

wherein $R_1$ is an alkylene group having 1 to 6 carbon atoms, which may have a methyl group,
X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$R_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—,
wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;
L represents —$(CH_2)_d$—[$R_3$—$(CH_2)_e$]$_f$— or —[$(CH_2)_e$—$R_3$]$_f$—$(CH_2)_d$—, wherein $R_3$ is an oxygen atom, a sulfur atom, —NH—, —NH—(C=O)—, or —(C=O)—NH—;
TAG is a tag;
a and c are identical or different and each represents an integer of 0 to 6;
b is 0 or 1;
d and e are identical or different and each represents an integer of 0 to 12; and
f is an integer of 0 to 24.

18. The method according to claim 17, wherein the complex is formed on the solid phase in the forming step.

19. A method for measuring a signal from a complex comprising a cholesterol, comprising the steps of:
forming the complex by contacting:
a lipoprotein in a sample;
a tagged cholesterol;
an antibody which specifically binds to the lipoprotein; and
a labeled capture body comprising the label and the capture body,
wherein the complex comprises the lipoprotein, the tagged cholesterol, the antibody and the labeled capture body, and
wherein the capture body specifically binds to a tag of the tagged cholesterol in the complex;
detecting a signal resulted from the label which has been bound to the complex,
wherein the tagged cholesterol is represented by the following formula (III):

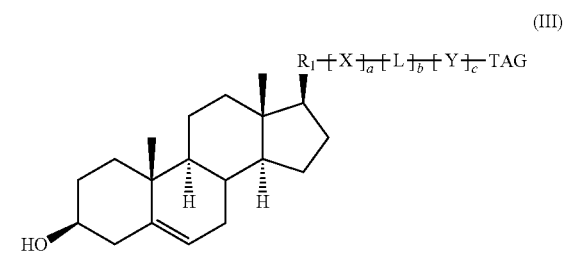

(III)

wherein $R_1$ is an alkylene group having 1 to 6 carbon atoms, which may have a methyl group,
X and Y are identical or different and each represents —$R_2$—NH—, —NH—$R_2$—, —$R_2$—(C=O)—NH—, —(C=O)—NH—$R_2$—, —$R_2$—NH—(C=O)—, —NH—(C=O)—$R_2$—, —$R_2$—(C=O)—, —(C=O)—$R_2$—, —$R_2$—(C=O)—O—, —(C=O)—O—$R_2$—, —$R_2$—O—(C=O)—, —O—(C=O)—$R_2$—, —$R_2$—(C=S)—NH—, —(C=S)—NH—$R_2$—, —$R_2$—NH—(C=S)—, —NH—(C=S)—$R_2$—, —$R_2$—O—, —O—$R_2$—, —$R_2$—S—, or —S—$R_2$—,
wherein each $R_2$ is independently an atomic bonding; an alkylene group having 1 to 10 carbon atoms, which may have a substituent group; an arylene group or a heteroarylene group having 6 to 12 carbon atoms, each of which may have a substituent group; or a cycloalkylene group or a heterocycloalkylene group having 3 to 8 carbon atoms, each of which may have a substituent group;
L represents —$(CH_2)_d$—[$R_3$—$(CH_2)_e$]$_f$— or —[$(CH_2)_e$—$R_3$]$_f$—$(CH_2)_d$—, wherein $R_3$ is an oxygen atom, a sulfur atom, —NH—, —NH—(C=O)—, or —(C=O)—NH—;
TAG is a tag;
a and c are identical or different and each represents an integer of 0 to 6;
b is 0 or 1;
d and e are identical or different and each represents an integer of 0 to 12; and
f is an integer of 0 to 24.

* * * * *